(12) United States Patent
Alexandroni et al.

(10) Patent No.: US 11,627,924 B2
(45) Date of Patent: Apr. 18, 2023

(54) SYSTEMS AND METHODS FOR IMAGE-GUIDED NAVIGATION OF PERCUTANEOUSLY-INSERTED DEVICES

(71) Applicant: Covidien LP, Mansfield, MA (US)

(72) Inventors: Guy Alexandroni, Haifa (IL); Oren P. Weingarten, Hod-Hasharon (IL); Evgeni Kopel, Barkan (IL)

(73) Assignee: COVIDIEN LP, Mansfield, MA (US)

( * ) Notice: Subject to any disclaimer, the term of this patent is extended or adjusted under 35 U.S.C. 154(b) by 271 days.

(21) Appl. No.: 17/013,107

(22) Filed: Sep. 4, 2020

(65) Prior Publication Data

US 2021/0085268 A1    Mar. 25, 2021

Related U.S. Application Data

(60) Provisional application No. 62/905,151, filed on Sep. 24, 2019.

(51) Int. Cl.
*A61B 6/12* (2006.01)
*A61B 90/00* (2016.01)
(Continued)

(52) U.S. Cl.
CPC ............. *A61B 6/12* (2013.01); *A61B 6/466* (2013.01); *A61B 6/487* (2013.01); *A61B 6/5205* (2013.01);
(Continued)

(58) Field of Classification Search
CPC .............. A61B 34/10; A61B 17/3403; A61B 2090/3764; A61B 90/11; A61B 2034/107; A61B 10/04; A61B 34/20; A61B 5/062; A61B 5/065; A61B 6/032; A61B 6/463; A61B 6/466; A61B 6/487; A61B 6/5205; A61B 6/5235; A61B 2010/045; A61B 2090/3966; A61B 6/12; A61B 90/06; A61B 90/39; A61B 90/37; A61B 90/92; A61B 34/25; A61B 6/4405; A61B 6/4441; A61B 6/56; A61B 5/743; A61B 6/025; A61B 6/465; A61B 5/1073; A61B 5/6852; A61B 6/00; A61B 2017/00809; A61B 2034/105;
(Continued)

(56) References Cited

U.S. PATENT DOCUMENTS 5,057,494 A    10/1991    Sheffield
5,321,113 A    6/1994    Cooper et al.
(Continued)

FOREIGN PATENT DOCUMENTS

BR    0013237 A    7/2003
BR    0116004 A    6/2004
(Continued)

OTHER PUBLICATIONS

Extended European search report issued in European Application No. 20198223.8 dated Dec. 9, 2020, 13 pages.
(Continued)

*Primary Examiner* — Irakli Kiknadze
(74) *Attorney, Agent, or Firm* — Weber Rosselli & Cannon LLP

(57) ABSTRACT

Systems and methods for image-guided medical procedures use fluoroscopic 3D reconstructions to plan and navigate a percutaneously-inserted device such as a biopsy tool from an entry point to a target.

20 Claims, 10 Drawing Sheets

(51) Int. Cl.
    *A61B 6/00*         (2006.01)
    *A61B 6/03*         (2006.01)
    *A61B 34/10*       (2016.01)
    *A61B 34/20*       (2016.01)
    *A61B 6/02*         (2006.01)

(52) U.S. Cl.
    CPC ............ *A61B 6/5235* (2013.01); *A61B 90/06* (2016.02); *A61B 90/39* (2016.02); *A61B 6/022* (2013.01); *A61B 6/032* (2013.01); *A61B 34/10* (2016.02); *A61B 34/20* (2016.02); *A61B 2034/107* (2016.02); *A61B 2034/2051* (2016.02); *A61B 2034/2065* (2016.02); *A61B 2090/062* (2016.02); *A61B 2090/367* (2016.02); *A61B 2090/376* (2016.02)

(58) Field of Classification Search
    CPC .... A61B 2034/2046; A61B 2034/2048; A61B 2034/2051; A61B 2034/2065; A61B 2090/367; A61B 2090/376; A61B 2090/3762; A61B 2090/3908; A61B 2090/3983; A61B 6/488; A61B 2090/062; A61B 2090/3995; A61B 6/022; A61B 6/464; A61B 34/70; A61B 5/0071; A61B 6/547; A61B 6/584; A61B 6/486; G06T 11/003; G06T 7/337; G06T 7/70; G06T 19/003; G06T 7/0012; G06T 2207/10121; G06T 2210/22; G06T 2210/41; G06T 2211/424; G06T 7/344; G06T 3/005; G06T 15/005
    USPC .................................. 600/424; 378/4, 42, 62
    See application file for complete search history.

(56) References Cited

U.S. PATENT DOCUMENTS

| | | | |
|---|---|---|---|
| 5,930,329 | A | 7/1999 | Navab |
| 5,963,613 | A | 10/1999 | Navab |
| 6,003,517 | A | 12/1999 | Sheffield et al. |
| 6,484,049 | B1 | 11/2002 | Seeley et al. |
| 7,233,820 | B2 | 6/2007 | Gilboa |
| 8,165,660 | B2 | 4/2012 | Pfister et al. |
| 8,335,359 | B2 | 12/2012 | Fidrich et al. |
| 8,542,900 | B2 | 9/2013 | Tolkowsky et al. |
| 8,694,075 | B2 * | 4/2014 | Groszmann ............ A61B 6/488 |
| | | | 382/128 |
| 8,706,184 | B2 | 4/2014 | Mohr et al. |
| 8,827,934 | B2 | 9/2014 | Chopra et al. |
| 9,265,468 | B2 * | 2/2016 | Rai ........................ A61B 6/547 |
| 9,375,268 | B2 | 6/2016 | Long |
| 9,918,659 | B2 | 3/2018 | Chopra et al. |
| 10,004,558 | B2 | 6/2018 | Long |
| 10,154,239 | B2 * | 12/2018 | Casas ....................... G06F 3/011 |
| 10,194,897 | B2 | 2/2019 | Cedro et al. |
| 10,373,719 | B2 | 8/2019 | Soper et al. |
| 10,376,178 | B2 | 8/2019 | Chopra |
| 10,405,753 | B2 | 9/2019 | Sorger |
| 10,478,162 | B2 | 11/2019 | Barbagli et al. |
| 10,480,926 | B2 | 11/2019 | Froggatt et al. |
| 10,524,866 | B2 | 1/2020 | Srinivasan et al. |
| 10,555,788 | B2 | 2/2020 | Panescu et al. |
| 10,569,071 | B2 | 2/2020 | Harris et al. |
| 10,603,106 | B2 | 3/2020 | Weide et al. |
| 10,610,306 | B2 | 4/2020 | Chopra |
| 10,638,953 | B2 | 5/2020 | Duindam et al. |
| 10,639,114 | B2 | 5/2020 | Schuh et al. |
| 10,674,970 | B2 | 6/2020 | Averbuch et al. |
| 10,674,982 | B2 | 6/2020 | Barak et al. |
| 10,682,070 | B2 | 6/2020 | Duindam |
| 10,702,137 | B2 | 7/2020 | Deyanov |
| 10,706,543 | B2 | 7/2020 | Donhowe et al. |
| 10,709,506 | B2 | 7/2020 | Coste-Maniere et al. |
| 10,716,525 | B2 | 7/2020 | Weingarten et al. |
| 10,772,485 | B2 | 9/2020 | Schlesinger et al. |
| 10,796,432 | B2 | 10/2020 | Mintz et al. |
| 10,823,627 | B2 | 11/2020 | Sanborn et al. |
| 10,827,913 | B2 | 11/2020 | Ummalaneni et al. |
| 10,835,153 | B2 | 11/2020 | Rafii-Tari et al. |
| 10,885,630 | B2 | 1/2021 | Li et al. |
| 2002/0147462 | A1 | 10/2002 | Mair et al. |
| 2003/0013972 | A1 | 1/2003 | Makin |
| 2004/0120981 | A1 | 6/2004 | Nathan |
| 2005/0222554 | A1 | 10/2005 | Wallace et al. |
| 2008/0045938 | A1 | 2/2008 | Weide et al. |
| 2008/0097187 | A1 | 4/2008 | Gielen et al. |
| 2008/0123921 | A1* | 5/2008 | Gielen ...................... G06T 7/32 |
| | | | 382/175 |
| 2008/0154526 | A1 | 6/2008 | Li et al. |
| 2008/0161684 | A1 | 7/2008 | Li et al. |
| 2010/0215213 | A1 | 8/2010 | Mielekamp et al. |
| 2013/0303945 | A1 | 11/2013 | Blumenkranz et al. |
| 2014/0035798 | A1 | 2/2014 | Kawada et al. |
| 2015/0042643 | A1 | 2/2015 | Shibata et al. |
| 2015/0148690 | A1 | 5/2015 | Chopra et al. |
| 2015/0265368 | A1 | 9/2015 | Chopra et al. |
| 2016/0000517 | A1 | 1/2016 | Kehat et al. |
| 2016/0157939 | A1 | 6/2016 | Larkin et al. |
| 2016/0183841 | A1 | 6/2016 | Duindam et al. |
| 2016/0192860 | A1 | 7/2016 | Allenby et al. |
| 2016/0287344 | A1 | 10/2016 | Donhowe et al. |
| 2017/0035380 | A1 | 2/2017 | Barak et al. |
| 2017/0112571 | A1 | 4/2017 | Thiel et al. |
| 2017/0112576 | A1 | 4/2017 | Coste-Maniere et al. |
| 2017/0209071 | A1 | 7/2017 | Zhao et al. |
| 2017/0265952 | A1 | 9/2017 | Donhowe et al. |
| 2017/0311844 | A1 | 11/2017 | Zhao et al. |
| 2017/0319165 | A1 | 11/2017 | Averbuch |
| 2018/0078318 | A1 | 3/2018 | Barbagli et al. |
| 2018/0144092 | A1 | 5/2018 | Flitsch et al. |
| 2018/0153621 | A1 | 6/2018 | Duindam et al. |
| 2018/0235709 | A1 | 8/2018 | Donhowe et al. |
| 2018/0240237 | A1 | 8/2018 | Donhowe et al. |
| 2018/0256262 | A1 | 9/2018 | Duindam et al. |
| 2018/0263706 | A1 | 9/2018 | Averbuch |
| 2018/0279852 | A1 | 10/2018 | Rafii-Tari et al. |
| 2018/0325419 | A1 | 11/2018 | Zhao et al. |
| 2019/0000559 | A1 | 1/2019 | Berman et al. |
| 2019/0000560 | A1 | 1/2019 | Berman et al. |
| 2019/0005687 | A1* | 1/2019 | Weingarten ............. G06T 19/00 |
| 2019/0008413 | A1 | 1/2019 | Duindam et al. |
| 2019/0038365 | A1 | 2/2019 | Soper et al. |
| 2019/0065209 | A1 | 2/2019 | Mishra et al. |
| 2019/0110839 | A1 | 4/2019 | Rafii-Tari et al. |
| 2019/0175062 | A1 | 6/2019 | Rafii-Tari et al. |
| 2019/0175799 | A1 | 6/2019 | Hsu et al. |
| 2019/0183318 | A1 | 6/2019 | Froggatt et al. |
| 2019/0183585 | A1 | 6/2019 | Rafii-Tari et al. |
| 2019/0183587 | A1 | 6/2019 | Rafii-Tari et al. |
| 2019/0192234 | A1 | 6/2019 | Gadda et al. |
| 2019/0209016 | A1 | 7/2019 | Herzlinger et al. |
| 2019/0209043 | A1 | 7/2019 | Zhao et al. |
| 2019/0216548 | A1 | 7/2019 | Ummalaneni |
| 2019/0239723 | A1 | 8/2019 | Duindam et al. |
| 2019/0239831 | A1 | 8/2019 | Chopra |
| 2019/0250050 | A1 | 8/2019 | Sanborn et al. |
| 2019/0254649 | A1 | 8/2019 | Walters et al. |
| 2019/0269470 | A1 | 9/2019 | Barbagli et al. |
| 2019/0269818 | A1 | 9/2019 | Dhanaraj et al. |
| 2019/0269819 | A1 | 9/2019 | Dhanaraj et al. |
| 2019/0272634 | A1 | 9/2019 | Li et al. |
| 2019/0298160 | A1 | 10/2019 | Ummalaneni et al. |
| 2019/0298451 | A1 | 10/2019 | Wong et al. |
| 2019/0320878 | A1 | 10/2019 | Duindam et al. |
| 2019/0320937 | A1 | 10/2019 | Duindam et al. |
| 2019/0336238 | A1 | 11/2019 | Yu et al. |
| 2019/0343424 | A1 | 11/2019 | Blumenkranz et al. |
| 2019/0350659 | A1 | 11/2019 | Wang et al. |
| 2019/0365199 | A1 | 12/2019 | Zhao et al. |
| 2019/0365479 | A1 | 12/2019 | Rafii-Tari |
| 2019/0365486 | A1 | 12/2019 | Srinivasan et al. |
| 2019/0380787 | A1 | 12/2019 | Ye et al. |

(56) References Cited

U.S. PATENT DOCUMENTS

| | | |
|---|---|---|
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 | 12/2008 |
| CZ | 186540 | 9/2016 |
| CZ | 2709512 | 8/2017 |
| CZ | 2884879 | 1/2020 |
| EP | 1774909 A1 | 4/2007 |
| EP | 1644519 B1 | 12/2008 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 | 2/2005 |
| MX | PA03010507 A | 7/2005 |
| MX | PA05011725 A | 5/2006 |
| MX | 06011286 | 3/2007 |
| MX | 246862 B | 6/2007 |
| MX | 2007006441 A | 8/2007 |
| MX | 265247 | 3/2009 |
| MX | 284569 B | 3/2011 |

OTHER PUBLICATIONS

Extended European Search Report issued in European Application No. 20198236.0 dated Dec. 8, 2020, 15 pages.

Arianna Ferrari et al., "Digital chest tomosynthesis: the 2017 updated review of an emerging application", Ann Transl Med 2018; 6(5): 91, pp. 1-8.

Nelson et al., "Improved targeting accuracy of lung tumor biopsies with scanning-beam digital x-ray tomosynthesis image guidance", Medical Physics, vol. 43, No. 12, Dec. 2016, 9 pages.

* cited by examiner

# SYSTEMS AND METHODS FOR IMAGE-GUIDED NAVIGATION OF PERCUTANEOUSLY-INSERTED DEVICES

FIELD

This disclosure relates to the field of image-guided navigation of medical devices, and particularly to image-guided navigation of percutaneously-inserted tools from a percutaneous entry point to a target (e.g., a tumor) to perform a procedure, for example, localization (e.g., using a dye, guide wire, or fiducials), biopsy, or ablation of the target.

BACKGROUND

Computed tomography (CT)-guided needle biopsy is a common method for obtaining tissue samples from lung nodules for lung cancer diagnosis. A patient lies on a CT table and receives a local anesthesia injection to numb the needle path. A target lung nodule is located through a pre-operative CT scan, which is used by a clinician to plan the safest needle path to the target nodule. Using intraoperative CT scans to confirm the positions of the target nodule and the needle, the clinician inserts the needle through the skin, advances it towards and into the target nodule, and removes samples of the target nodule. While CT provides high spatial resolution and good tissue contrast, which enables precise and safe placement of biopsy needles, CT does not provide real-time imaging, tracking, and movement perception.

SUMMARY

In aspects, this disclosure features methods of performing image-guided medical procedures using a percutaneously-inserted device. In aspects, the percutaneously-inserted medical device may be used for performing localization, biopsy, ablation, or any other suitable image-guided medical procedure. In one general aspect, this disclosure features a method of performing an image-guided medical procedure. The method includes performing a fluoroscopic sweep of at least a portion of a patient's body that includes a target area to obtain fluoroscopic images; determining a fluoroscopic pose for each of the fluoroscopic images; generating a fluoroscopic 3D reconstruction based on the fluoroscopic images and the fluoroscopic poses, and applying a trajectory of a percutaneously-inserted device to the fluoroscopic 3D reconstruction such that the fluoroscopic 3D reconstruction includes a planned trajectory. The method also includes displaying a live fluoroscopic image and overlaying the planned trajectory of the percutaneously-inserted device on the live fluoroscopic image. The method also includes displaying advancement of a percutaneously-inserted device a first distance in the live fluoroscopic image and determining at two angles that the advancement of the percutaneously-inserted device the first distance is following the planned trajectory. The method also includes displaying advancement of the percutaneously-inserted device a second distance in response to determining at two angles that the advancement of the percutaneously-inserted device the first distance is following the planned trajectory, and determining at two angles that the advancement of the percutaneously-inserted device the second distance is following the planned trajectory.

In aspects, implementations of this disclosure may include one or more of the following features. The method may include applying a mark indicating a critical structure to avoid to the fluoroscopic 3D reconstruction, and overlaying the mark indicating the critical structure to avoid on the live fluoroscopic image. The planned trajectory may include a target, an insertion point, and a line between the insertion point and the target. Performing the fluoroscopic sweep may include performing the fluoroscopic sweep to obtain fluoroscopic images of a radiopaque object. The method may include determining the position of the radiopaque object relative to the target and determining the position of an insertion point based on the position of the radiopaque object relative to the target. The fluoroscopic sweep may be performed after insertion of the percutaneously-inserted device at the insertion point.

The method may include determining that the percutaneously-inserted device is located at the target and performing one or more additional fluoroscopic sweeps to obtain one or more additional fluoroscopic images in response to determining that the percutaneously-inserted device is not located at the target.

The method may include receiving preoperative computed tomography (CT) images including markings indicating the planned trajectory. The method may include registering the fluoroscopic 3D reconstruction to the preoperative CT images. Applying a planned trajectory of the percutaneously-inserted device to the fluoroscopic 3D reconstruction may include transferring the markings on the preoperative CT images to the fluoroscopic 3D reconstruction based on the registering.

Registering may include determining one or more anatomical features that may be in both the fluoroscopic 3D reconstruction and the preoperative CT images. Registering may include aligning the fluoroscopic 3D reconstruction and the preoperative CT images based on the determined one or more anatomical features. The one or more anatomical features may include the target, a lesion, a tumor, or a rib.

In another general aspect, this disclosure features a method of performing an image-guided medical procedure. The method includes performing a first fluoroscopic sweep of at least a portion of a patient's body that includes a target area to obtain first fluoroscopic images, determining a pose for each of the first fluoroscopic images, and generating and displaying a first fluoroscopic 3D reconstruction based on the first fluoroscopic images and the poses. The method also includes marking a planned trajectory in the first fluoroscopic 3D reconstruction, displaying a live fluoroscopic image, and overlaying the planned trajectory on the live fluoroscopic image. The method also includes adjusting the live fluoroscopic image such that the trajectory appears as a point and advancing the percutaneously-inserted device along the planned trajectory based on the adjusted live fluoroscopic image.

In aspects, implementations of this disclosure may include one or more of the following features. The method may include displaying the length of the planned trajectory. The percutaneously-inserted device may be advanced based on the length of the planned trajectory and length markers on the percutaneously-inserted device. The planned trajectory may include an insertion point, a target, and a line between the insertion point and the target. The method may include adjusting the live fluoroscopic image to a second angle to verify the depth of the percutaneously-inserted device in the patient's body. The method may include adjusting the live fluoroscopic image to a third angle to verify the direction of the percutaneously-inserted device.

In another general aspect, this disclosure features a method of performing an image-guided medical procedure. The method includes performing a first fluoroscopic sweep of at least a portion of a patient's body that includes a target area to obtain first fluoroscopic images, determining a first fluoroscopic pose for each of the first fluoroscopic images, generating and displaying a first fluoroscopic 3D reconstruction based on the first fluoroscopic images and the first fluoroscopic poses. The method also includes applying a trajectory of a percutaneously-inserted device to the first fluoroscopic 3D reconstruction such that the first fluoroscopic 3D reconstruction includes a planned trajectory, displaying a live fluoroscopic image, and overlaying the planned trajectory of the percutaneously-inserted device on the live fluoroscopic image. The method also includes performing a second fluoroscopic sweep to obtain second fluoroscopic images of an insertion point, determining a second pose for each of the second fluoroscopic images, and generating and displaying a second fluoroscopic 3D reconstruction based on the second fluoroscopic images and the second poses. The method also includes displaying insertion of a percutaneously-inserted device in the live fluoroscopic image.

In aspects, implementations of this disclosure may include one or more of the following features. The method may include registering the second fluoroscopic 3D reconstruction to the first fluoroscopic 3D reconstruction and transferring the planned trajectory applied to the first fluoroscopic 3D reconstruction to the second fluoroscopic 3D reconstruction based on the registering. The method may include displaying the live fluoroscopic image in at least one fluoroscopic angle after advancement of the inserted percutaneously-inserted device a first distance, and determining that the advancement of the inserted percutaneously-inserted device the first distance is following the planned trajectory based on the live fluoroscopic image in the at least one fluoroscopic angle.

The at least one fluoroscopic angle may include two different fluoroscopic angles at which a direction of the inserted percutaneously-inserted device can be determined from the live fluoroscopic image.

The method may include displaying the live fluoroscopic image in at least one fluoroscopic angle after advancement of the inserted percutaneously-inserted device a second distance and determining that the advancement of the inserted percutaneously-inserted device the second distance is following the planned trajectory based on the live fluoroscopic image in the at least one fluoroscopic angle. The method may include performing a third fluoroscopic sweep to obtain third fluoroscopic images after advancement of the inserted percutaneously-inserted device the second distance, determining a third pose for each of the third fluoroscopic images; and generating and displaying a third fluoroscopic 3D reconstruction based on the third fluoroscopic images and the third poses.

BRIEF DESCRIPTION OF THE DRAWINGS

Various exemplary embodiments are illustrated in the accompanying figures with the intent that these examples are not restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

Figure 1A:
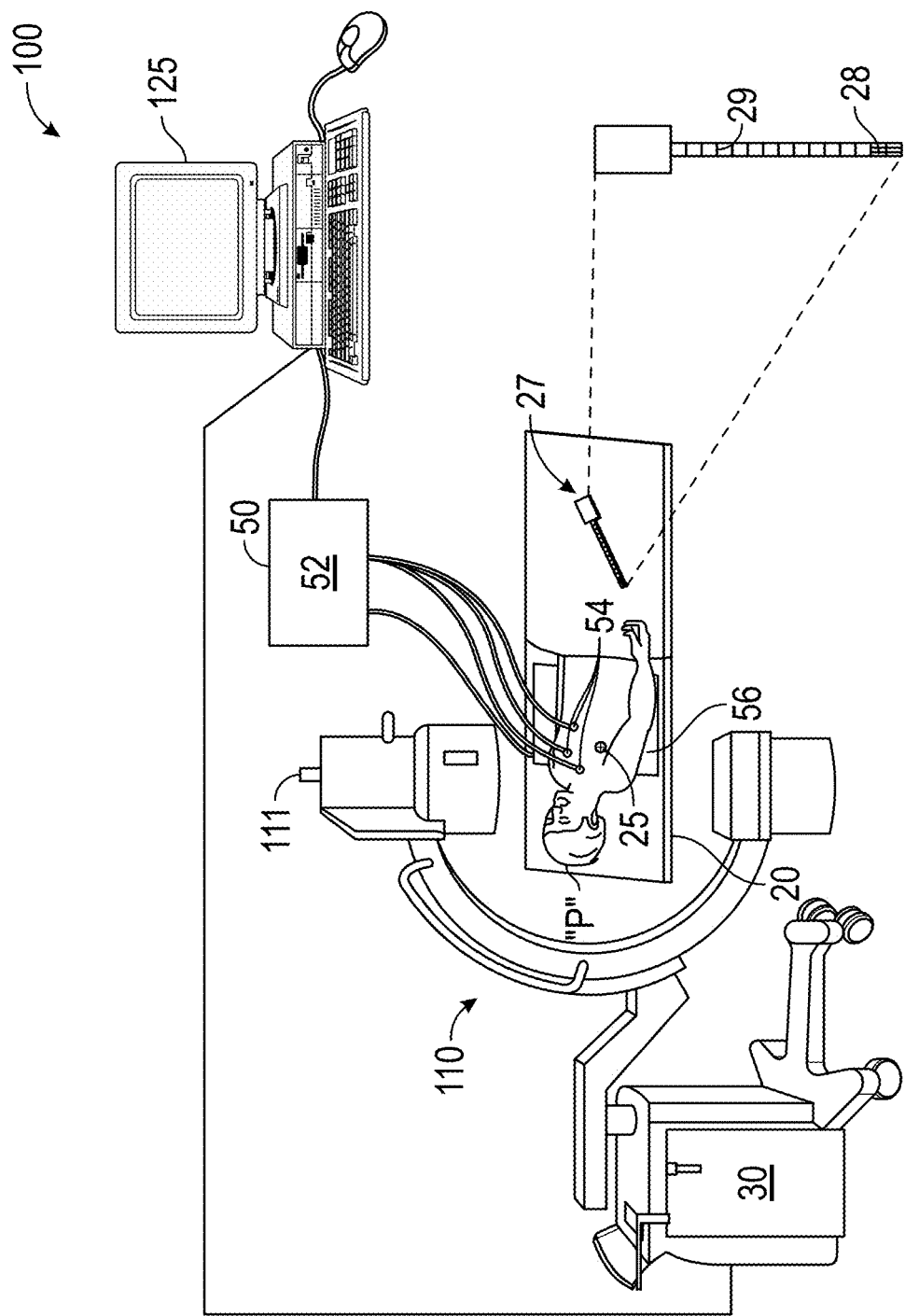
FIG. 1A is a schematic diagram of an exemplary system for performing image-guided navigation of a biopsy tool in accordance with aspects of this disclosure.

This disclosure relates to systems and methods for image-guided, e.g., fluoroscopy- and/or (electromagnetic) EM-guided, navigation of percutaneously-inserted devices, e.g., biopsy tools, treatment tools (e.g., ablation tools), or needles. An advantage of a fluoroscope is that a fluoroscope can provide a live view of the medical procedure, e.g., a biopsy procedure. However, a fluoroscope may provide images having a lower quality than computed tomography (CT) images, which provide good visualization via axial and coronal views. One way to solve this issue is to fuse or merge the live fluoroscopic images with the CT images by, for example, overlaying portions of the CT images on the fluoroscopic images or vice versa. For example, the fusion may show the CT images around the tool in a fluoroscopic 3D reconstruction because CT images show the pleura better than the fluoroscopic 3D reconstruction. Alternatively, the fusion may involve displaying the tool in the fluoroscopic 3D reconstruction in the CT images. In other aspects, once the fluoroscopic 3D reconstruction is aligned with the CT images, the target, e.g., lesion, from either the fluoroscopic 3D reconstruction or the CT images may be displayed in the fused or merged images.

Systems and methods according to aspects of the disclosure involve centering a fluoroscope on an estimated target location, performing a fluoroscopic sweep to obtain fluoroscopic images, e.g., coronal slices, and determining poses of the fluoroscopic images. A fluoroscopic 3D reconstruction may then be generated based on the fluoroscopic images and the poses and presented to a clinician. The fluoroscopic 3D reconstruction may be presented to the clinician as a series of fluoroscopic two-dimensional (2D) reconstruction images corresponding to slices of the fluoroscopic reconstruction. The clinician may plan a trajectory by placing one or more marks on the fluoroscopic 3D reconstruction or on the fluoroscopic 2D reconstruction images including an entry point mark (i.e., the location where the percutaneously-inserted device should be placed), a target mark, and/or a trajectory mark or line indicating a trajectory between the entry point and the target. The entry point, the target, and/or the trajectory may then be displayed in a live 2D fluoroscopy view based on the trajectory planned by the clinician. Alternatively, a navigation system may automatically plan a trajectory including the entry point based on the identification of the target. In aspects, the target, the entry point, the trajectory, and/or a structure to avoid may be selected or identified by the clinician, or automatically identified or segmented by the navigation system. Then, the target, the entry point, the trajectory, and/or a structure to avoid may be marked on a fluoroscopic 3D reconstruction and overlaid on the live 2D fluoroscopy image or in the EM navigation view.

As the clinician inserts and advances a percutaneously-inserted device towards the target while viewing the live 2D fluoroscopy image and the planned trajectory overlaid on the live 2D fluoroscopy image, additional fluoroscopic sweeps are performed to generate additional fluoroscopic 3D reconstructions. In the first sweep, one or more radiopaque objects (e.g., needles) may optionally be placed or laid on the patient such that the one or more radiopaque objects appear in the corresponding first fluoroscopic 3D reconstruction to understand the location of the entry point on the patient's body. Then, a needle is slightly inserted at the entry point based on the first fluoroscopic 3D reconstruction. In second or additional sweeps, after the needle is already introduced into the patient's body, the clinician checks the needle direction versus the trajectory to the target in the respective second or additional fluoroscopic 3D reconstructions that are displayed to the clinician. The clinician adjusts the needle direction each time and advances the needle further. In some aspects, if the clinician confirms that the direction of the needle is good after insertion, the distance to the target is calculated and displayed to the clinician so she can advance the needle the displayed distance in one action using length markers on the needle, and reach the target after the second sweep. In other aspects, the clinician confirms that the direction of the needle is good at different locations along the trajectory towards the target based on respective additional sweeps.

In aspects, a marked fluoroscopic 3D reconstruction is used in live two-dimensional (2D) fluoroscopy with an overlay. First, a planned trajectory, which is on a fluoroscopic 3D reconstruction and may include a target, an insertion point, and a line in between, is overlaid on the live 2D fluoroscopy view or image. Second, the clinician makes sure in two angles that the needle is inserted to follow the trajectory. For example, the needle is advanced in baby steps making sure in two angles that the direction of the needle is good, and then the needle is advanced in larger steps until the second angle verification.

Alternatively, the fluoroscope is adjusted to make the overlaid trajectory appear as a point (e.g., a bullseye view) in the live 2D fluoroscopy image, and then the needle is inserted to follow the trajectory while the clinician checks the direction of the needle using the live 2D fluoroscopy image at a second angle different from the initial or first angle of the live 2D fluoroscopy image. The distance from the needle tip to the target may be determined from trajectory markings on the first fluoroscopic 3D reconstruction based on the first sweep. Then, the clinician can insert and/or advance the needle the determined distance based on length markers disposed on the needle. Optionally, the clinician can check the depth of the needle by using the live 2D fluoroscopy image at a third angle. In aspects, the methods described above can be combined in various combinations, e.g., additional sweeps while inserting and/or advancing the needle that is guided by respective fluoroscopic 3D reconstructions overlaid on the live 2D fluoroscopy view or image.

In each fluoroscopic sweep, the percutaneously-inserted device may be visible in the live 2D fluoroscopic images. As such, the percutaneously-inserted device may be either marked by the clinician or segmented automatically. Also, the actual trajectory of the percutaneously-inserted device may be shown in the live fluoroscopy view. The actual trajectory of the percutaneously-inserted device may be shown together with the planned trajectory in the live fluoroscopy view. In some aspects, the clinician may start the tool at the bullseye (i.e., where the crosshairs of a needle insertion point are centered in a circle marking the target) and follow the trajectory in projections of the fluoroscopic 3D reconstruction that are convenient to the clinician.

In aspects, an electromagnetic (EM) sensor is disposed on the percutaneously-inserted device and EM navigation is used to guide the percutaneously-inserted device to the target. In this aspect, the fluoroscopic 3D reconstruction including marks indicating an insertion point, a target, and a path to the target is registered to the navigation 3D views. Next, the marks in the fluoroscopic 3D reconstruction are transferred to the navigation 3D views based on the registering. Then, the clinician uses the navigation 3D views to guide the insertion and advancement of the percutaneously-inserted device.

In aspects, the methods involve marking an entry point, a target, a trajectory, and/or a structure to avoid on preoperative CT images and registering the fluoroscopic 3D reconstruction to the preoperative CT images so that the markings may be transferred to and displayed in the fluoroscopic 3D reconstruction. A clinician and/or a software application may mark an entry point, a target, a trajectory, and/or a structure to avoid on the preoperative CT images. The clinician may center the live fluoroscopic view on an estimated target location and perform a fluoroscopic sweep. Then, a fluoroscopic 3D reconstruction is generated from the fluoroscopic sweep and registered to the preoperative CT images. The registration of the fluoroscopic 3D reconstruction to the preoperative CT images may be based either on intra-modality registration methods (e.g., the mutual information method) or on markers (e.g., the target or the tool may serve as a marker and may be identified by the clinician or automatically segmented or recognized).

The live fluoroscopy view may show where a percutaneously-inserted device should be inserted and the tool's trajectory towards the target. One or more additional sweeps are performed to capture additional fluoroscopic images, which are used to generate a fluoroscopic 3D reconstruction, in which the position of the tool is either marked by the clinician or segmented automatically. The clinician follows the planned trajectory in projections convenient to the clinician. The actual trajectory of the tool is then shown in the preoperative CT images and/or in the fluoroscopic 3D reconstruction.

In aspects, the navigation system may determine where to percutaneously insert the tool and the trajectory to the target based on preoperative CT images, on a fluoroscopic 3D reconstruction, and/or on the live fluoroscopic image. Then, the clinician navigates the percutaneously-inserted device to the target in 3D, e.g., using the location of the tool obtained from a location sensor (e.g., EM sensor) of the tool or automatically determining the location of the tool based on the fluoroscopic 3D reconstruction from a grayscale calculation or any other suitable image processing method. Optionally, additional sweeps may be performed. After each fluoroscopic sweep, a new fluoroscopic 3D reconstruction may be generated and registered to the previous fluoroscopic 3D reconstruction and the navigation system may be updated. After navigation of the percutaneously-inserted device to the target, the additional fluoroscopic sweeps may be used to confirm whether the percutaneously-inserted device or the tip of the percutaneously-inserted device has reached the target.

FIG. 1A depicts an aspect of a navigation and image system 100 configured for reviewing or viewing fluoroscopy and/or CT image data to identify one or more targets, plan a pathway to an identified target (planning phase), navigate a biopsy needle 27 or other percutaneously-inserted device to a target (navigation phase) via a user interface, and confirming placement of the biopsy needle 27 (or any portion of the biopsy needle 27) relative to the target. The navigation and image system 100 may utilize an electromagnetic navigation system, a shape matching system, or any other suitable navigation and image system. The target may be tissue of interest or a region of interest identified during review of the fluoroscopy and/or CT image data during the planning phase. Following navigation, the tool may be used to obtain a tissue sample from the tissue located at, or proximate to, the target.

The navigation and image system 100 generally includes an operating table or bed 20 configured to support a patient "P;" a tracking system 50 including a tracking module 52, reference sensors 54 and a transmitter mat 56; a biopsy tool 27 or other percutaneously-inserted device, a location sensor 28 disposed on the biopsy tool 27, and a computing device 125 including software and/or hardware used to facilitate identification of a target, pathway planning to the target, navigation of the biopsy tool 27 to the target, and confirmation of the placement of the biopsy tool 27 relative to the target. The computing device 125 may include a video display for displaying a live fluoroscopic view including a live fluoroscopic image captured by the fluoroscopic imaging device 110, a fluoroscopic 3D reconstruction, fluoroscopic 2D reconstruction images, and/or preoperative CT images.

A fluoroscopic imaging device 110 capable of acquiring fluoroscopic or x-ray images or video of the patient "P" is also included in aspects of the navigation and image system 100. The images, series of images, or video captured may be stored within the fluoroscopic imaging device 110 or transmitted to computing device 125 for storage, processing, and display. Additionally, the fluoroscopic imaging device 110 may move relative to the patient "P" so that images may be acquired from different angles or perspectives relative to the patient "P" to create a fluoroscopic video. Fluoroscopic imaging device 110 may include an angle measurement device 111 which is configured to measure the angle of the fluoroscopic imaging device 110 relative to the patient "P." Angle measurement device 111 may be an accelerometer. Fluoroscopic imaging device 110 may include a single imaging device or more than one imaging device. In aspects including multiple imaging devices, each imaging device may be a different type of imaging device or the same type.

Computing device 125 may be any suitable computing device including a processor and storage medium, wherein the processor is capable of executing instructions stored on the storage medium. The computing device 125 is operably coupled to some or all of the components of the navigation and image system 100 including tracking system 50. The computing device 125 may include a database configured to store patient data, CT data sets including CT images and volumetric renderings, fluoroscopic data sets including fluoroscopic images and video, navigation plans, and any other such data. Although not explicitly illustrated, the computing device 125 may include inputs, or may otherwise be configured to receive, CT data sets, fluoroscopic images/video and other data described herein. Additionally, computing device 125 includes a display configured to display graphical user interfaces described herein. Computing device 125 may be connected to one or more networks through which one or more databases may be accessed.

With respect to the planning phase, computing device 125 utilizes fluoroscopy images and/or previously acquired CT images to enable the identification of an entry point at which the biopsy tool 27 enters patient P's body percutaneously and a target on either or both of those images (automatically, semi-automatically, or manually), and allows for determining a pathway or trajectory from the entry point to tissue located at and/or around the target. The fluoroscopic and/or CT images may be displayed on a display associated with computing device 125, or in any other suitable fashion.

With respect to the navigation phase according to one aspect, a five degrees-of-freedom or a six degrees-of-freedom electromagnetic tracking system 50 or other suitable positioning measuring system may be utilized for performing navigation of the biopsy tool 27, although other configurations are also contemplated. Tracking system 50 includes a tracking module 52, reference sensors 54, a transmitter mat 56, and the location sensor 28 disposed on the biopsy tool 27. Length markers 29 may also be disposed on the biopsy tool 27 to assist with navigation as described herein. For example, systems of this disclosure may determine a distance from the tip of the biopsy tool 27 to the target based on fluoroscopic images. Then, the biopsy tool 27 may be advanced the determined distance using the length markers 29.

Transmitter mat 56 is positioned beneath patient "P." Transmitter mat 56 generates an electromagnetic field around at least a portion of the patient "P" within which the position of the reference sensors 54 and the location sensor 28 can be determined with use of a tracking module 52. One or more of reference sensors 54 are attached to the chest of the patient "P." The six degrees of freedom coordinates of reference sensors 54 are sent to computing device 125 (which may be a computing device storing and executing appropriate software) where they are used to calculate a patient coordinate frame of reference. Registration, as detailed herein, is generally performed to align the fluoroscopic 3D reconstruction with the previously acquired CT images.

Previously acquired CT scans, may not provide a basis sufficient for accurate guiding of the biopsy needle 27 or other percutaneously-inserted device to a target during a biopsy or other medical procedure. The inaccuracy may be caused by CT-to-Body divergence (deformation of the patient's lungs during the procedure relative to the lungs at the time of the acquisition of the previously acquired CT data). Thus, another imaging modality is needed to visualize targets and confirm placement of the biopsy needle 27 during a biopsy procedure. For this purpose, the system described herein processes image data captured by the imaging device 110 and/or CT image data as is described herein. This fluoroscopic image data may be utilized to identify targets and be incorporated into, and used to update, the data from the CT scans with, among other things, the actual trajectory of the biopsy needle 27.

Figure 1B:
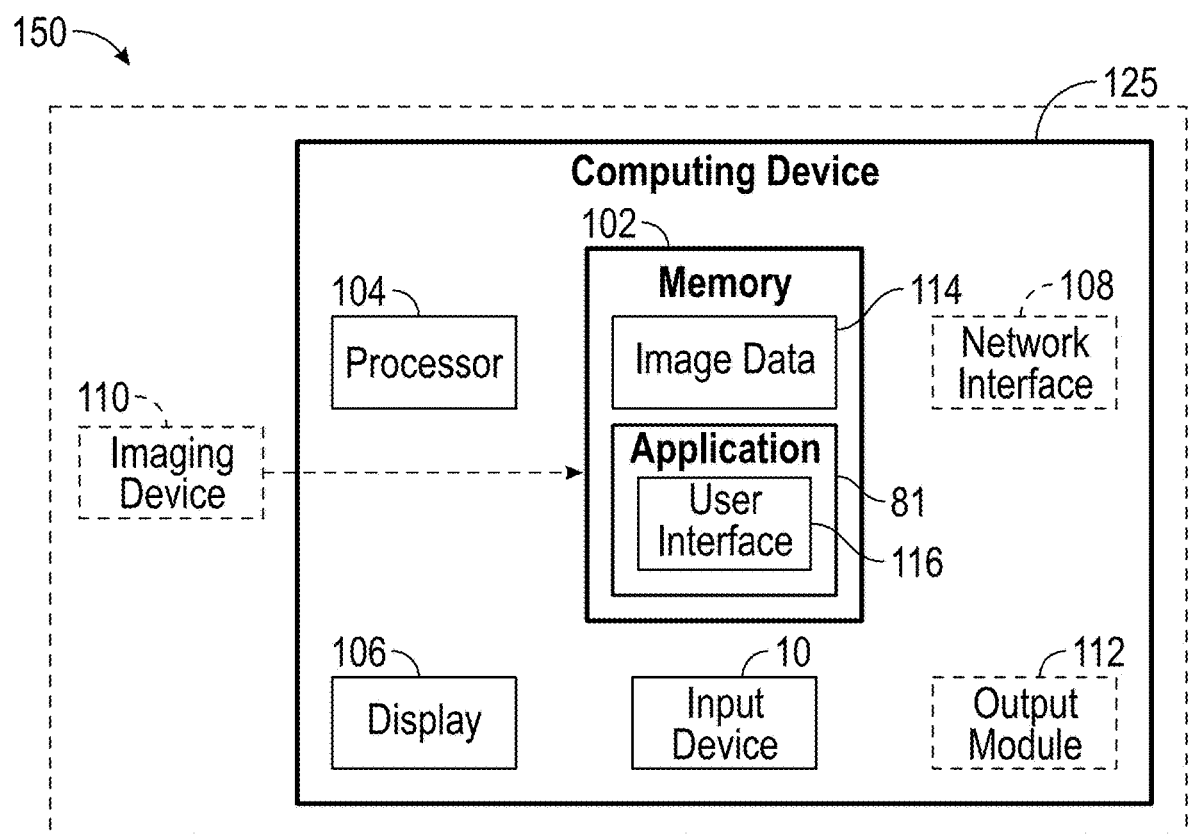
FIG. 1B is a schematic diagram of a system configured for use with the methods and user interfaces of this disclosure.

Reference is now made to FIG. 1B, which is a schematic diagram of a system 150 configured for use with the methods and user interfaces described herein. System 150 may include a computing device 125, and an imaging device 110, such as a fluoroscopic imaging device or fluoroscope. In some aspects, computing device 125 may be coupled with imaging device 110, directly or indirectly, e.g., by wireless communication. Computing device 125 may include memory 102 (e.g., a storage device), a processor 104, a display 106 and an input device 10. Processor or hardware processor 104 may include one or more hardware processors. Computing device 125 may optionally include an output module 112 and a network interface 108.

Memory 102 may store an application 81 and image data 114. Application 81 may include instructions executable by processor 104 for, among other functions, executing the methods of FIGS. 5-7 as described herein. Application 81 may further include a user interface 116. Image data 114 may include the 3D imaging such as pre-operative CT images, the fluoroscopic 3D reconstruction of the target area, and/or any other fluoroscopic image data, e.g., one or more fluoroscopy images. Processor 104 may be coupled with memory 102, display 106, input device 10, output module 112, network interface 108, and imaging device 110 (e.g., a fluoroscope). Computing device 125 may be a stationary computing device, such as a personal computer, or a portable computing device such as a tablet computer. Computing device 125 may embed one or more computing devices.

Memory 102 may include any non-transitory computer-readable storage media for storing data and/or software including instructions that are executable by processor 104 and which control the operation of computing device 125 and in some embodiments, may also control the operation of imaging device 110. Imaging device 110 may be used to capture a sequence of fluoroscopic images based on which the fluoroscopic 3D reconstruction is generated. In an aspect, storage device or memory 102 may include one or more storage devices such as solid-state storage devices such as flash memory chips. Alternatively, or in addition to the one or more solid-state storage devices, memory 102 may include one or more mass storage devices connected to the processor 104 through a mass storage controller (not shown) and a communications bus (not shown).

Although the description of computer-readable media contained herein refers to a solid-state storage, it should be appreciated by those skilled in the art that computer-readable storage media can be any available media that can be accessed by the processor 104. That is, computer readable storage media may include non-transitory, volatile, and non-volatile, removable, and/or non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by computing device 125, which may be a personal computer or workstation.

Application 81 may, when executed by processor 104, cause display 106 to present user interface 116. User interface 116 may be configured to present to the user the F3DR, two-dimensional fluoroscopic images, images of the 3D imaging and virtual fluoroscopy image, as shown, for example, in the exemplary screen shots of FIGS. 2A-2C, 3, and 4. User interface 116 may be further configured to direct the user to select a needle entry point (i.e., the point at which the needle percutaneously enters the patient's body) and the target by, among other methods or techniques, identifying and marking the needle entry point and the target in the displayed fluoroscopic 3D reconstruction or in any other fluoroscopic image data in accordance with aspects of this disclosure.

Network interface 108 may be configured to connect to a network such as a local area network (LAN) consisting of a wired network and/or a wireless network, a wide area network (WAN), a wireless mobile network, a Bluetooth network, and/or the internet. Network interface 108 may be used to connect between computing device 125 and imaging device 110, e.g., a fluoroscope. Network interface 108 may be also used to receive image data 114. Input device 10 may be any device by means of which a user may interact with computing device 125, such as, for example, a mouse, keyboard, foot pedal, touch screen, and/or voice interface. Output module 112 may include any connectivity port or bus, such as, for example, parallel ports, serial ports, universal serial busses (USB), or any other similar connectivity port known to those skilled in the art.

Figure 2A:
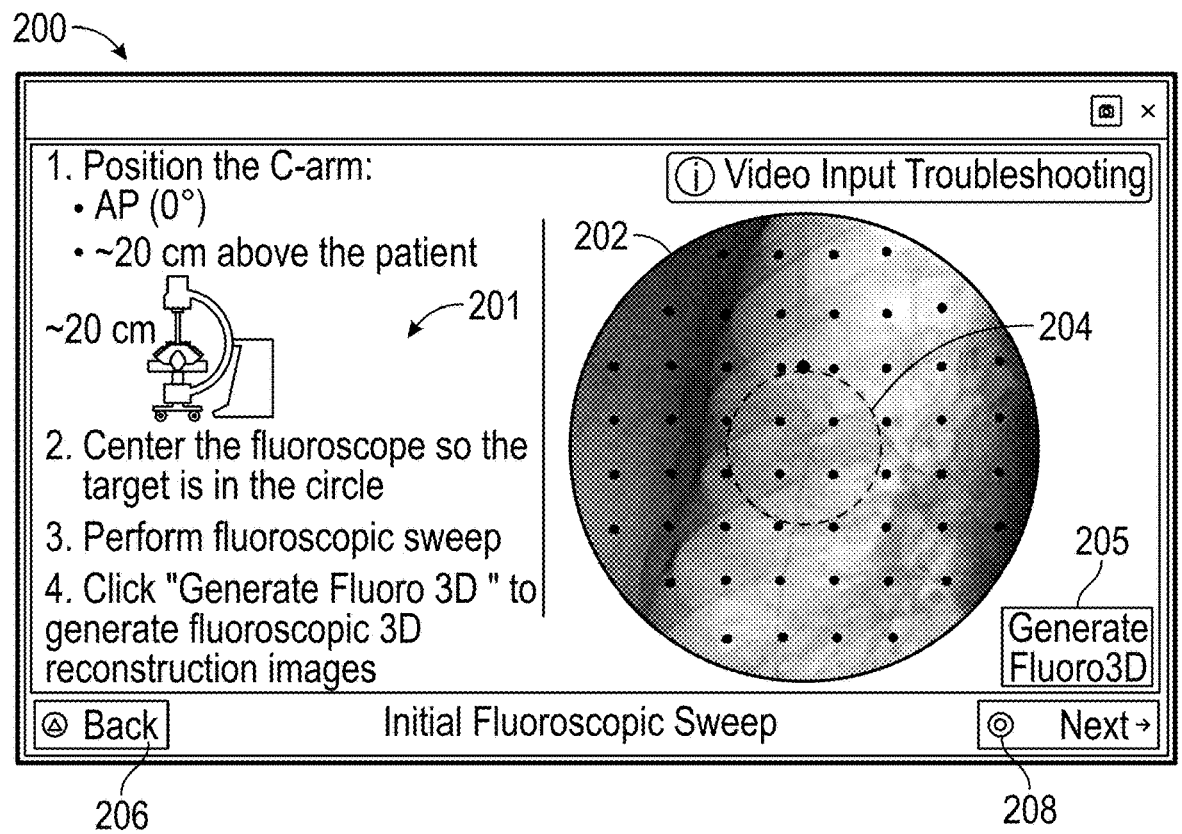
FIGS. 2A-2C illustrate user interfaces for performing a fluoroscopy-guided biopsy procedure in accordance with some aspects of this disclosure.
Figure 2B:
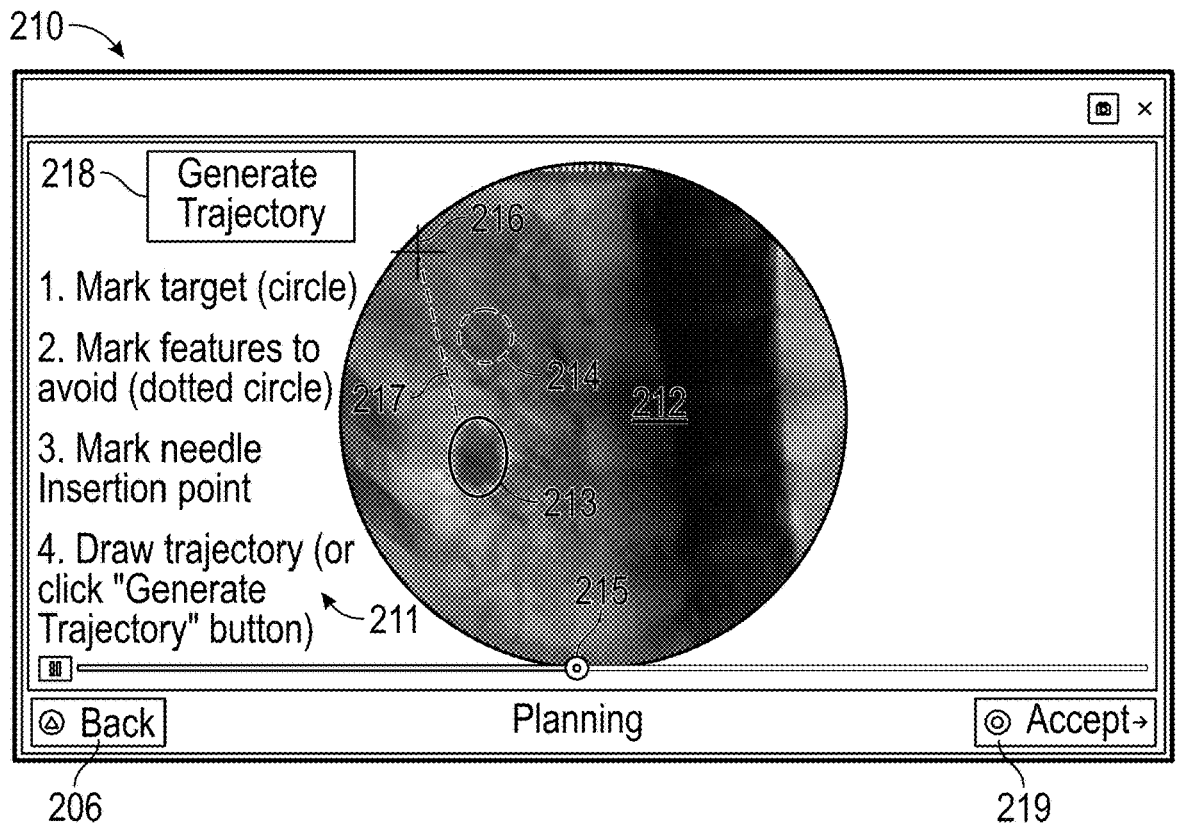
Figure 2C:
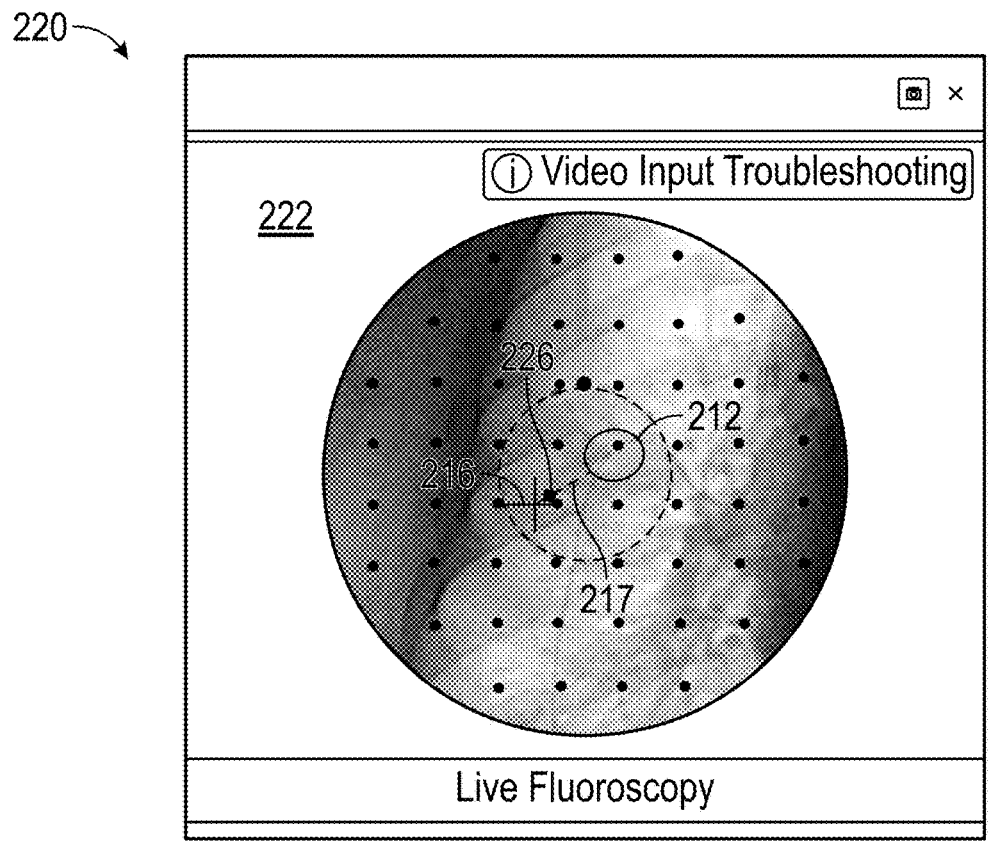
Figure 2C:
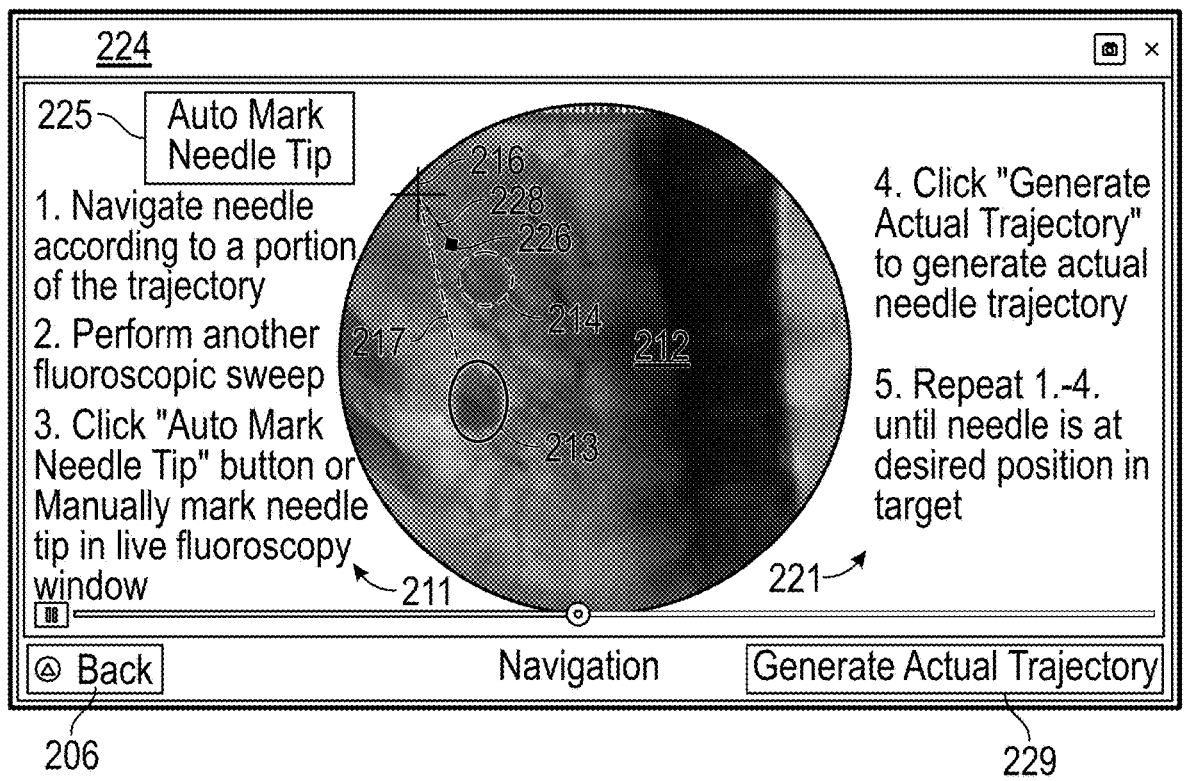

FIGS. 2A-2C depict user interfaces that may be used in conjunction with a fluoroscopy-guided medical procedures in accordance with aspects of this disclosure. The user interface 200 of FIG. 2A includes a user instruction area including user instructions 201 and a live fluoroscopy image area including a live fluoroscopic image 202. As illustrated in FIG. 2A, the user instructions 201 include an instruction to position the C-arm of the fluoroscope at the anterior-posterior view position, e.g., 0 degrees. The user instructions 201 may include another instruction to position the fluoroscope so that the target or estimated target is located or centered in the circle 204 drawn on or otherwise applied to the live fluoroscopic image 202. The user instructions 201 may include placing a radiopaque object on the patient's body at a possible entry point or near the target in order to determine an entry point for initial insertion of the biopsy needle. The user instructions 201 may include a further instruction to perform a fluoroscopic sweep after positioning the fluoroscope and optionally placing the radiopaque object on the patient's body.

The user instructions 201 may include a further instruction to click the "Generate Fluoro 3D" button 205 to generate a fluoroscopic 3D reconstruction, which is displayed in the planning user interface 210 of FIG. 2B for planning the trajectory of the biopsy needle. The user interface 200 includes a "Back" button 206 to return to a previous user interface, e.g., a setup interface. The user interface 200 also includes a "Next" button 208 to proceed to the next user interface, which may be the planning user interface 210 illustrated in FIG. 2B.

The planning user interface 210 of FIG. 2B includes user instructions 211 and a fluoroscopic 3D reconstruction 212, slices of which may be scrolled through by clicking and dragging the user control 215 either to the left or to the right. As illustrated in FIG. 2B, the user instructions 211 include an instruction to mark the target with a circle. In aspects, the clinician may mark one or more targets on the fluoroscopic 3D reconstruction 212. The target mark 213 may be a circle or any other suitable shape for marking the target. In some aspects, only the target mark 213 is overlaid on the live fluoroscopic image 202, and the clinician can place the biopsy needle between the ribs and use the live fluoroscopy window 222 to guide the biopsy needle to the target. As the biopsy needle is guided to the target, additional fluoroscopic sweeps may be performed to determine whether the biopsy needle needs to be tilted or otherwise repositioned or redirected. Alternatively, the fluoroscope may be moved to one or more other angles such that the clinician can confirm with the live fluoroscopic image 202 that the biopsy needle is positioned in a direction suitable for reaching the target.

Optionally, the user instructions 211 may include another instruction to mark one or more features that the biopsy needle must avoid with a dotted circle, e.g., dotted circle 214. The one or more features may include anatomical features such as one or more bones, one or more vascular structures, one or more nerve structures, or one or more critical structures, which, if punctured or damaged by the biopsy needle, would cause unnecessary bleeding or harm to the patient. As another option, the user instructions 211 may include a further instruction to mark where to puncture the patient with the needle, i.e., the needle insertion or entry point. The needle insertion point may be marked with crosshairs 216. In other aspects, an entry point may be automatically or manually marked based on determined and/or marked positions of the target and the radiopaque object.

Optionally, the user instructions 211 may include a further instruction to draw a trajectory 217 from the marked needle insertion point to the marked target on the fluoroscopic 3D reconstruction 212. In aspects, the user instructions 211 may include a further instruction to click an optional "Generate Trajectory" button 218 to automatically generate or plan a trajectory from the marked needle insertion point to the marked target and draw or otherwise apply the generated trajectory on the fluoroscopic 3D reconstruction 212.

In aspects, the planning user interface 210 may also allow a clinician to mark the angles of the biopsy tool with respect to the operating table and other rigid structures on the fluoroscopic 3D reconstruction 212 to provide guidance on the trajectory. There may be an intermediate instruction of injecting a substance, e.g., a dye, in the pleura or other body structure. Also, the clinician may be instructed to paint the entry point (e.g., bullseye 25 of FIG. 1A) on the body with a marker. In other aspects, one or more of the marks described herein may be alternatively applied to one or more frames of fluoroscopic images obtained from the initial fluoroscopic sweep.

The planning user interface 210 includes the "Back" button 206 to return to the initial fluoroscopic sweep user interface 200 illustrated in FIG. 2A. The planning user interface 210 also includes an "Accept" button 219 to accept the marks on the fluoroscopic 3D reconstruction 212 and to display the next user interface, which may include two windows: a live fluoroscopy window 222 and a navigation window 224 as illustrated in FIG. 2C. Alternatively, the live fluoroscopy window 222 and the navigation window 224 may be combined into a single window. The navigation window 224 includes the fluoroscopic 3D reconstruction 212, user instructions 221, an "Auto Mark Needle Tip" button 225, and a "Generate Actual Trajectory" button 229.

The user instructions 221 include an instruction to navigate the biopsy needle along a portion of the planned trajectory 217 starting at the needle entry point 216. The user instructions 221 include another instruction to perform another fluoroscopic sweep. In some aspects, the other fluoroscopic sweep is a narrower fluoroscopic sweep than the initial fluoroscopic sweep. In other aspects, the another and subsequent fluoroscopic sweeps while navigating the biopsy tool towards the target may be replaced by a 2D fluoroscopic snapshot in order to minimize the patient's exposure to radiation. In aspects, the 2D fluoroscopic snapshots could be taken lateral to the planned trajectory. For example, if the planned trajectory is perpendicular to the bed 20, the fluoroscopic snapshots could be taken at the lateral side. The fluoroscopic snapshots may be taken after each time the biopsy tool is moved a short distance.

The user instructions 221 include a further instruction to click the "Auto Mark Needle Tip" button 225 or to manually mark the biopsy needle tip 226 in the live fluoroscopy window 222. When the "Auto Mark Needle Tip" button 225 is clicked, an image recognition algorithm may process the live fluoroscopic image in the live fluoroscopy window 222 to identify or detect the biopsy needle tip 226 in the live fluoroscopic image.

The user instructions 221 may include a further instruction to click the "Generate Actual Trajectory" button 229 to generate or draw the actual needle trajectory 228 in both the live fluoroscopy window 222 and the navigation window 224. Alternatively, the actual needle trajectory 228 may be applied to or drawn in only the live fluoroscopy window 222 or the navigation window 224. The user instructions 221 include a further instruction to repeat instructions 1-4 until the biopsy needle tip 226 is at a desired position in the target indicated by the target mark 213. As illustrated in the live fluoroscopy window 222 and the navigation window 224, the actual trajectory 229 is not aligned with the planned trajectory 217. In this scenario, the clinician may remove the biopsy needle and retry puncturing the patient's skin with the biopsy needle and perform an initial navigation of the biopsy needle along the planned trajectory 217. Alternatively, the clinician may adjust the navigation direction of the biopsy needle for the next portion of the planned trajectory 217 so that the actual trajectory of the biopsy needle can come into more alignment with the planned trajectory 217.

Figure 3:
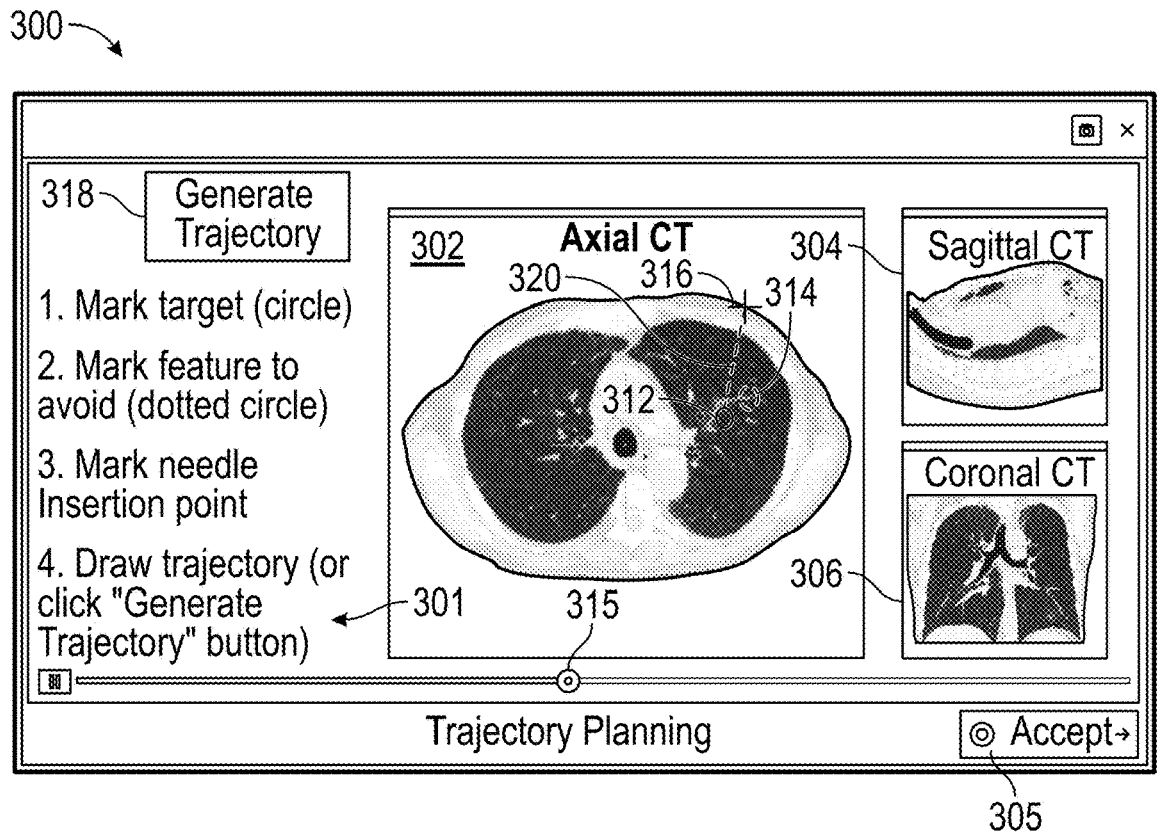
FIGS. 3 and 4 illustrate user interfaces for performing a fluoroscopy-guided biopsy procedure in accordance with other aspects of this disclosure.

FIG. 3 depicts a trajectory planning user interface 300 that utilizes computed tomography (CT) images to accurately identify a target and plan a path or trajectory to the target. The trajectory planning user interface 300 may be displayed instead of the user interface 200 of FIG. 2A. The trajectory planning may be performed by marking the target, the features to avoid, and/or the needle insertion point on preoperative CT images, and either automatically generating a trajectory from the needle insertion point to the target or manually drawing a trajectory on the preoperative CT images. As illustrated in FIG. 3, the trajectory planning user interface 300 includes user instructions 301 and three CT windows: An Axial CT window 302, which is illustrated as the main CT window in FIG. 3, a Sagittal CT window 304, and a Coronal CT window 306. Any one of the CT windows 302, 304, 306 may be displayed as the main CT window by, for example, clicking and dragging one of the smaller CT windows 304, 306 into the area of the main CT window, which may cause the Axial CT window 302 to shrink to the smaller size and to move to the rightmost part of the trajectory planning user interface 300. The CT images or slices of the main CT window may be scrolled through by clicking and dragging the user control 315 either to the left or to the right.

As illustrated in FIG. 3, the user instructions 301 include an instruction to mark the target with a circle. In aspects, the clinician may mark one or more targets on the Axial CT window 302. The target mark 312 may be a circle or any other suitable shape for marking the target. The user instructions 301 may include another instruction to mark one or more features or structures, e.g., anatomical features, that the biopsy needle must avoid with a dotted circle 314. The user instructions 301 may include a further instruction to mark the needle insertion point. The needle insertion point may be marked with crosshairs 316. The user instruction 301 may include a further instruction to (1) manually draw a trajectory 320 from the marked needle insertion point to the marked target on the Axial CT window 302 or (2) click the "Generate Trajectory" button 318 to automatically generate or plan a trajectory from the marked needle insertion point to the marked target and draw the generated trajectory on the Axial CT window 302.

Then, an initial fluoroscopic sweep may be performed, the fluoroscopic 3D reconstruction may be generated based on the initial fluoroscopic sweep data, and the fluoroscopic 3D reconstruction may be registered to the preoperative CT images. The registration process enables biopsy needle information (e.g., the biopsy needle's actual trajectory) obtained from fluoroscopy sweeps to be shown on the preoperative CT images. In performing the registration between the fluoroscopic 3D reconstruction and the CT images, the clinician may be prompted to mark a lesion, ribs, or other body structure in both the fluoroscopic 3D reconstruction and in the CT images.

Figure 4:
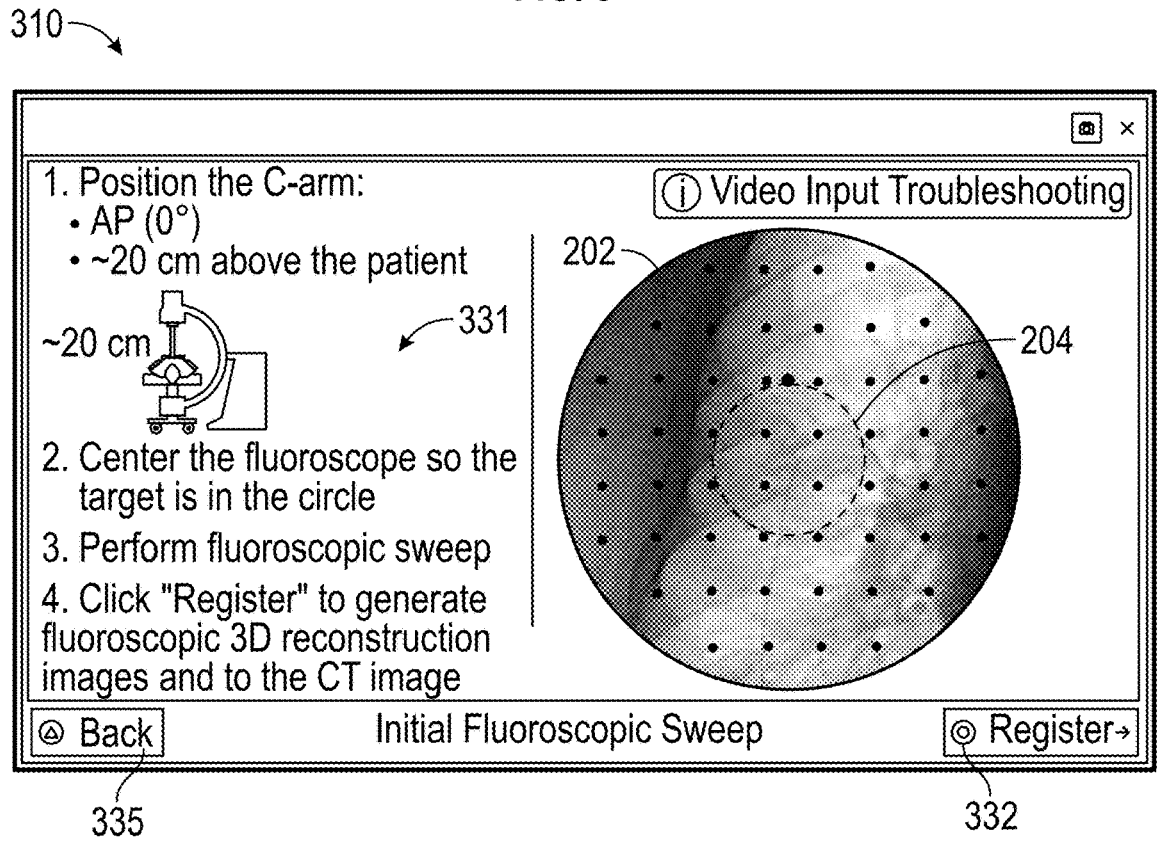

FIG. 4 illustrates a trajectory planning user interface 310 for implementing such fluoroscopic 3D reconstruction and registration features as part of an initial fluoroscopic sweep workflow. The trajectory planning user interface 310 includes user instructions 301 and a live fluoroscopic image 202. The user instructions 301 include an instruction to position the C-arm of the fluoroscope at the anterior-posterior view position, e.g., 0 degrees. The user instructions 301 may include another instruction to position the fluoroscope so that the target or estimated target is located or centered in the circle 204 on the live fluoroscopic image 202. The user instructions 301 may include a further instruction to perform a fluoroscopic sweep after positioning the fluoroscope. The user instructions 301 may include a further instruction to click the "Register" button 332 to generate fluoroscopic 3D reconstruction images and to register the fluoroscopic 3D reconstruction images to the CT images illustrated in FIG. 3. Then, the marks applied to the CT images may be transferred to the fluoroscopic 3D reconstruction so that needle navigation may be performed using the marked fluoroscopic 3D reconstruction. The trajectory user interface 200 includes a "Back" button 335 to return to a previous user interface, e.g., the trajectory planning user interface 300 of FIG. 3.

Figure 5:
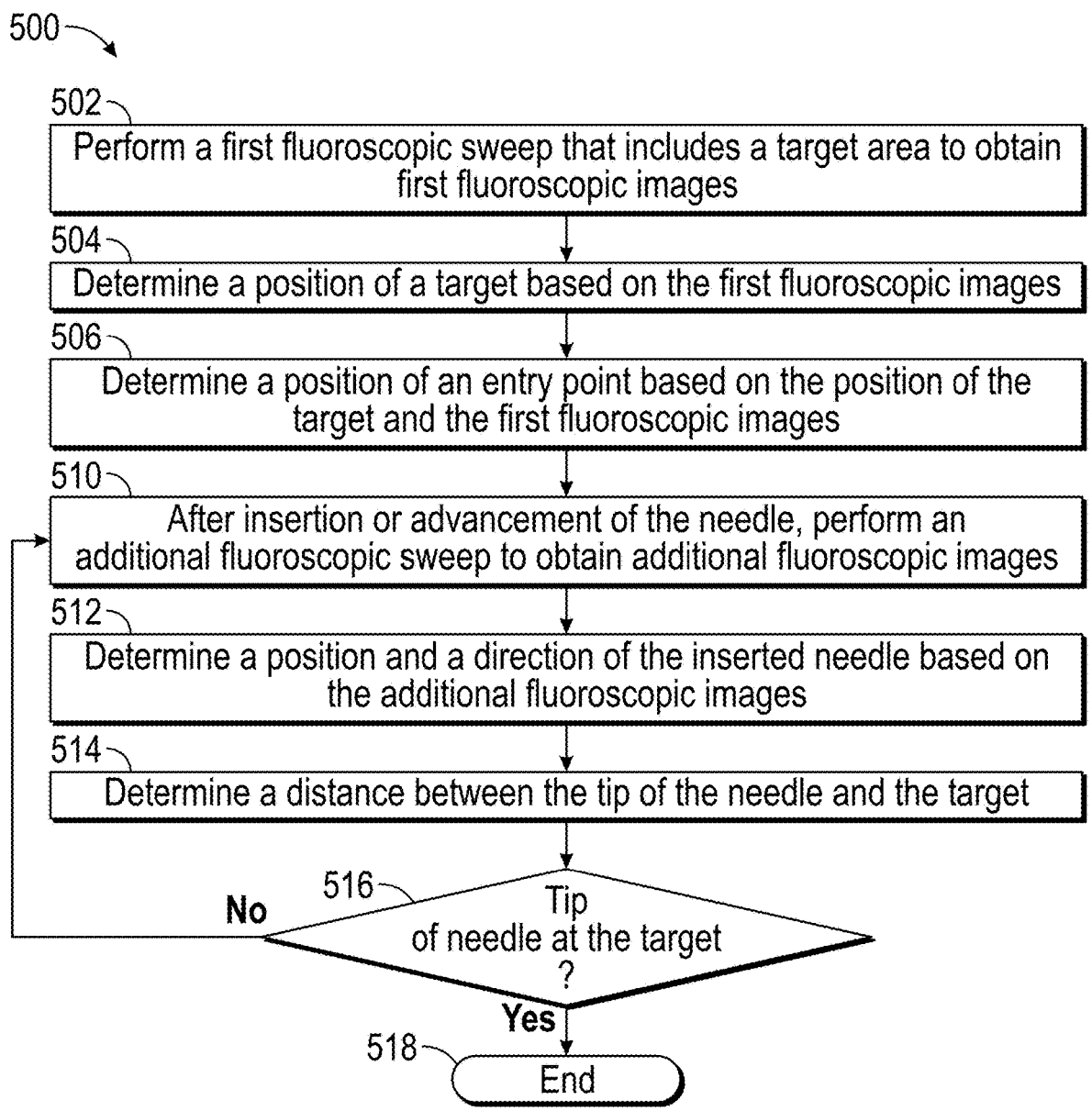
FIGS. 5 and 6 are flowcharts of methods for performing a fluoroscopy-guided medical procedure in accordance with aspects of this disclosure.

FIG. 5 is a flowchart of a method for performing an image-guided medical procedure in accordance with an aspect of this disclosure. At block 502, a first fluoroscopic sweep of at least a portion of the patient's body that includes a target area is performed to capture multiple first fluoroscopic images. The target or target area may be centered in the live fluoroscopy view before performing the first fluoroscopic sweep. The first fluoroscopic sweep may include rotating a fluoroscopic imaging device about or around at least a portion of the patient's body, e.g., rotating a fluoroscopic imaging device at least 30 degrees around at least a portion of the patient's body. Before performing block 502, the method may include centering a live fluoroscopic image captured by a fluoroscopic imaging device at a fixed angle, e.g., at 0 degrees, perpendicular to the bed 20, or at 5 degrees, at a current time.

In aspects, the position of the target and the entry point may be determined from a first fluoroscopic 3D reconstruction generated based on the first fluoroscopic images. In some aspects, block 502 may further include determining a pose for each of the captured first fluoroscopic images and generating a first fluoroscopic 3D reconstruction is generated based on the captured first fluoroscopic images and the poses. Then, the first fluoroscopic 3D reconstruction may be displayed in a trajectory planning window. In some aspects, the first fluoroscopic 3D reconstruction may be "cut" into slices to obtain "2D-like" images, which may be displayed and scrolled through by a clinician, e.g., by clicking and dragging the user control 215 of FIG. 2B either to the left or to the right. The first fluoroscopic 3D reconstruction may be displayed in a trajectory planning window, in which, for example, the clinician may mark or otherwise draw a planned trajectory from an entry point to a target on the fluoroscopic 3D reconstruction, or click a button to automatically generate a planned trajectory from the entry point to the target in the fluoroscopic 3D reconstruction.

In some aspects, one or more marks indicating the entry point (e.g., a bullseye), the target, a trajectory to the target, and/or one or more structures to avoid, are applied to the fluoroscopic 3D reconstruction, and the marked first fluoroscopic 3D reconstruction is displayed. The one or more marks may include crosshairs, lines, shapes, or any other suitable marks for indicating the insertion point, the target, the trajectory, and/or the one or more structures to avoid. In some aspects, at least one of the target and the needle shown in the first fluoroscopic 3D reconstruction may be identified and at least one mark indicating at least one of the target and the needle may be applied to the first fluoroscopic 3D reconstruction. Identifying the needle in the first fluoroscopic reconstruction may include receiving a mark indicating a location of the needle on the first fluoroscopic 3D reconstruction, for example, through a user interface or controls operated by a clinician. Identifying the needle in the first fluoroscopic 3D reconstruction may include segmenting the first fluoroscopic 3D reconstruction to determine a location of the needle. In aspects, the needle may be a biopsy needle or an ablation device.

At block 504, a position of a target is determined based on the first fluoroscopic images. Then, at block 506, a position of an entry point is determined based on the position of the target and the first fluoroscopic images.

At block 510, after the needle is inserted into or advanced through the patient's body, an additional fluoroscopic sweep is performed to capture multiple additional fluoroscopic images. In some aspects, block 510 may include determining poses for each of the additional fluoroscopic images, generating an additional fluoroscopic 3D reconstruction based on the additional fluoroscopic images and the poses for each of the additional fluoroscopic images, and displaying the additional fluoroscopic 3D reconstruction. Block 510 may further include registering the current fluoroscopic 3D reconstruction to a previous fluoroscopic 3D reconstruction, and transferring the one or more marks applied to the previous fluoroscopic 3D reconstruction to the current fluoroscopic 3D reconstruction based on the registering. Performing the additional fluoroscopic sweeps may include performing a second fluoroscopic sweep. Performing the first fluoroscopic sweep may include performing the second fluoroscopic sweep to obtain first fluoroscopic images of one or more objects, which may include a metal grid or any suitable radiopaque object. Then, the position of the one or more objects relative to the target may be determined. In turn, the position of the entry point may be determined based on the position of the one or more objects relative to the target.

At block 512, the position and the direction of the inserted needle is determined based on the additional fluoroscopic images. Then, at block 514, a distance between the tip of the needle and the target is determined. In aspects, the distance between the needle and the target may be calculated based on the additional fluoroscopic 3D reconstruction. Then, the distance may be displayed to the clinician and the needle may be advanced the displayed distance by the clinician using length markers on the needle to reach the target with the tip of the needle.

At block 516, the method 500 determines whether the tip of the needle has reached a desired location in the target. If the tip of the needle has not reached the desired location in the target, the method 500 returns to block 510 to perform an additional fluoroscopic sweep to obtain additional fluoroscopic images. Optionally, additional poses for each of the additional fluoroscopic images may be determined and additional fluoroscopic 3D reconstructions may be generated based on the additional fluoroscopic images and the additional poses. Blocks 510-516 are repeated until the tip of the needle has reached the target. If the tip of the needle has reached the target, the method 500 ends at block 518.

Figure 6:
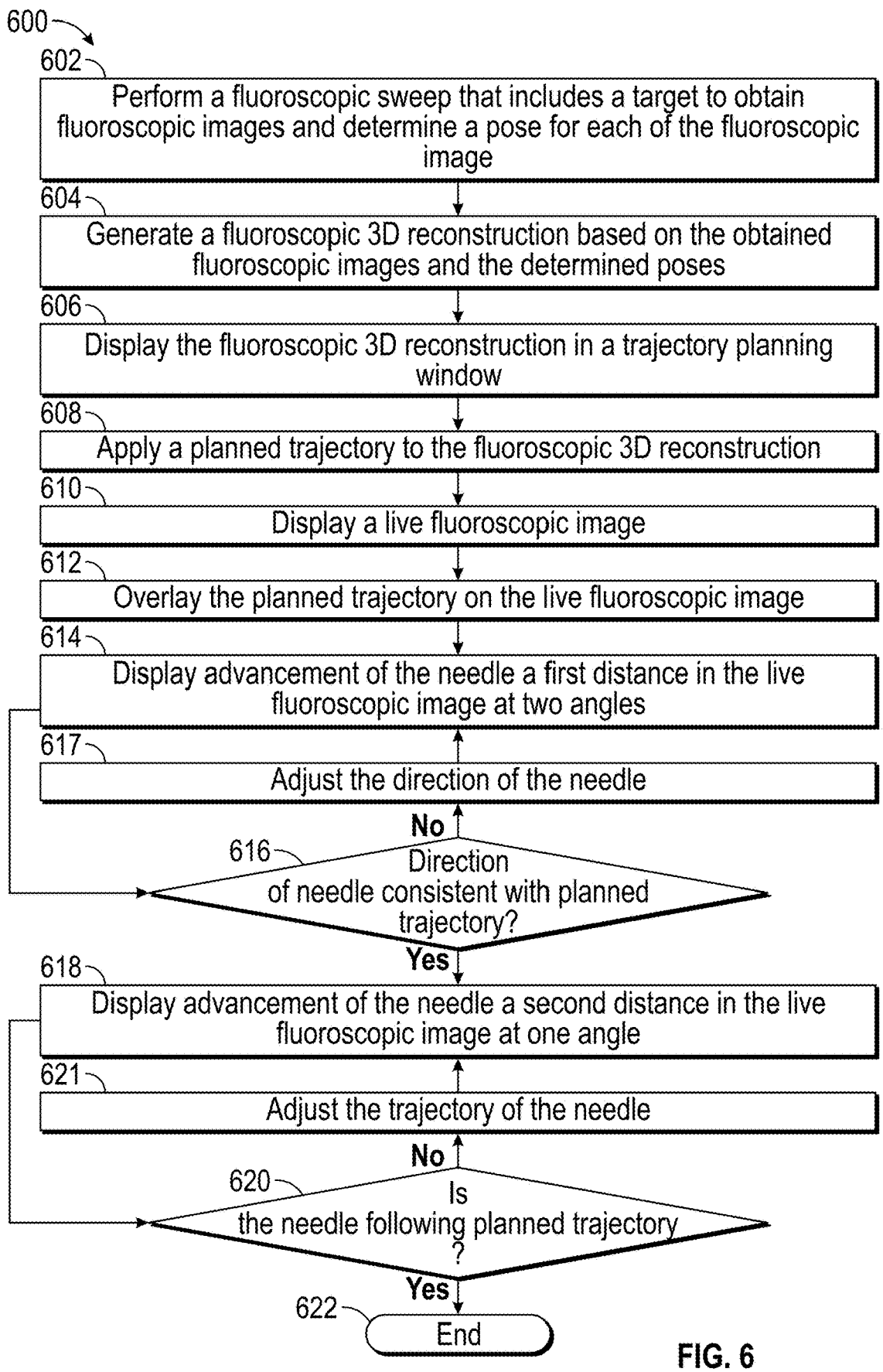

FIG. 6 is a flowchart of a method for performing an image-guided medical procedure in accordance with another aspect of this disclosure. At block 602, a fluoroscopic sweep of at least a portion of the patient's body that includes a target area is performed to capture multiple fluoroscopic images and a pose for each of the multiple fluoroscopic images is determined. The fluoroscopic sweep may be performed after the percutaneously-inserted device is inserted at an insertion point. The position of the insertion point may be determined based on the position of the target. For example, the fluoroscopic sweep may be performed to obtain fluoroscopic images of a radiopaque object placed on the patient at or near a possible insertion point. Then, the position of the insertion point may be determined based on the position of the radiopaque object relative to the target.

At block 604, a fluoroscopic 3D reconstruction is generated based on the captured fluoroscopic images and the poses determined at block 602. Then, at block 606, the fluoroscopic 3D reconstruction is displayed. At block 608, a planned trajectory is applied to the fluoroscopic 3D reconstruction. The planned trajectory may include a target, an insertion point, and a line between the insertion point and the target. In some aspects, a mark indicating a critical structure to avoid may also be applied to the fluoroscopic 3D reconstruction.

At block 610, a live fluoroscopic image, which includes a view of a needle, is displayed and, at block 612, the planned trajectory, which may be indicated by one or more marks are overlaid or displayed on the live fluoroscopic image. The live fluoroscopic image may be displayed in a live fluoroscopy view or window. The live fluoroscopy view may display projections that enable the clinician to guide or navigate a needle so that the needle follows the planned trajectory to the target.

In aspects, a mark indicating a critical structure to avoid may also be applied to the fluoroscopic 3D reconstruction and the mark indicating the critical structure to avoid may be overlaid on the live fluoroscopic image. In aspects, the marks indicating the insertion point, the target, and the critical structure to avoid may be obtained from preoperative CT images. The method 600 may include receiving marked preoperative CT images, registering the fluoroscopic 3D reconstruction to the preoperative CT images, and transferring the markings on the preoperative CT images to the fluoroscopic 3D reconstruction based on the registering. The registering may include determining anatomical features that are in both the fluoroscopic 3D reconstruction and the preoperative CT images, and aligning the fluoroscopic 3D reconstruction and the preoperative CT images based on the anatomical features. The anatomical features may include the target, a lesion, a tumor, or a rib.

At block 614, the advancement of the needle a first distance is displayed in the live fluoroscopic image at two angles. The live fluoroscopic image at two angles provides a view of the direction of the needle. At block 616, the method 600 determines whether the direction of the needle in the live fluoroscopic image is consistent with the planned trajectory overlaid on the live fluoroscopic image. If the direction of the needle is not consistent with the planned trajectory, the direction of the needle is adjusted at block 617 and blocks 614 and 616 are repeated. In some aspects, the needle may be adjusted at block 617 by retracting the needle a small distance before repeating blocks 614 and 616.

If the direction of the needle is consistent with the planned trajectory, advancement of the needle a second distance is displayed in the live fluoroscopic image at one angle, e.g., one of the two angles of block 614 that shows the depth of the needle, at block 618. In aspects, the first distance may be less than the second distance so that one or more small advancement steps are taken to confirm that the needle is advancing in the direction of the planned trajectory before advancing the needle in larger advancement steps towards the target. At block 620, the method 600 determines whether the needle is following the planned trajectory. If the needle is not following the planned trajectory, the trajectory of the needle is adjusted at block 621 and blocks 618 and 620 are repeated until the needle is following the planned trajectory. If the needle is following the planned trajectory, the method 600 ends at block 622.

In aspects, before ending at block 622, the method 600 may include determining whether that the needle is located at the target, and performing one or more additional fluoroscopic sweeps to obtain one or more additional fluoroscopic images in response to determining that the needle is not located at the target. These functions may be repeated until the needle is determined to be located at the target.

The planned trajectory may include an entry point, a target, and a path between the entry point and the target. In aspects, the needle is any percutaneously-inserted device suitable for performing, for example, localization (e.g., using a dye, guide wire, or fiducials), biopsy (e.g., a biopsy needle), or ablation of the target. The actual trajectory of the tip of the needle may be determined by receiving a marking by a clinician or other user of the needle tip on the additional fluoroscopic 3D reconstruction. Alternatively, obtaining the location of the medical device in the additional fluoroscopic images includes automatically segmenting the additional fluoroscopic images to determine the location of the medical device.

Figure 7:
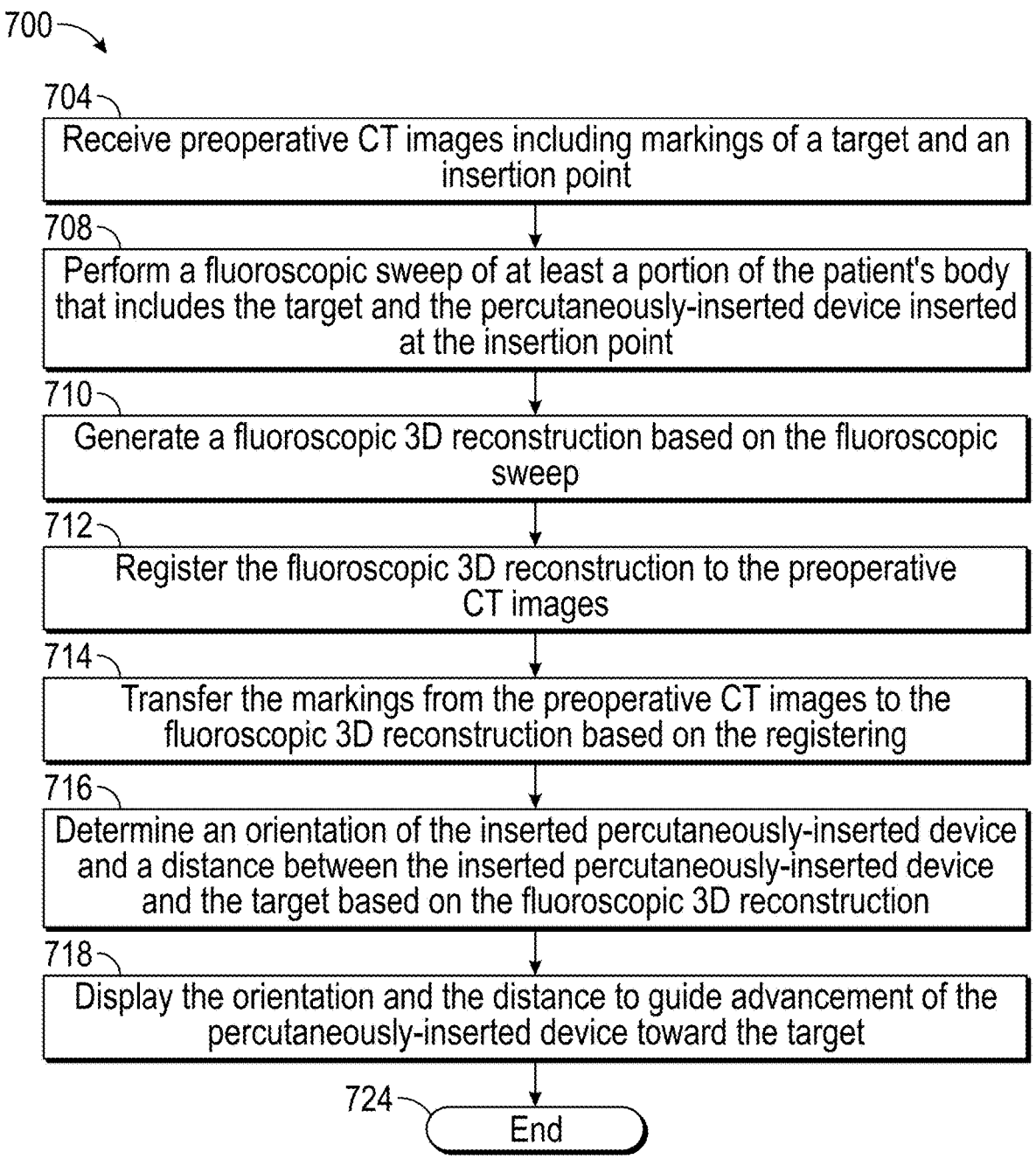
FIG. 7 is a flowchart of a method for planning a fluoroscopy-guided medical procedure utilizing computed tomography (CT) images in accordance with other aspects of this disclosure.

FIG. 7 is a flowchart of a method 700 for performing a fluoroscopy-guided medical procedure utilizing computed tomography (CT) images in accordance with an aspect of this disclosure. At block 704, preoperative CT images including markings of a target and an insertion point are received. In aspects, the preoperative CT images may also include markings of a trajectory and/or one or more structures to avoid. In aspects, the method 700 may include generating a trajectory between the marks. In aspects, the method 700 may include receiving marks indicating a target and a structure to avoid and generating and displaying an insertion point and a trajectory so that the trajectory avoids the structure to avoid. The markings may be received in response to selection of the target, the insertion point, the trajectory, and/or one or more structures to avoid by the navigation and image system 100 or by a clinician.

In some aspects, a 3D CT reconstruction or 3D volume rendering is generated based on the CT images and a trajectory is applied to the 3D CT reconstruction either by a clinician drawing the trajectory on or otherwise applying the planned trajectory to the 3D CT reconstruction or a software application automatically drawing the planned trajectory on the 3D CT reconstruction. The 3D CT reconstruction may be displayed to a clinician in a suitable user interface. Subsequently, the 3D CT reconstruction may be updated based on the fluoroscopic 3D reconstruction generated at block 710. For example, the actual trajectory of a biopsy device may be updated in the 3D CT reconstruction. The 3D CT reconstruction may provide more detail than the fluoroscopic 3D reconstruction, which, for example, better enables a clinician not to hit an anatomic feature to be avoided with the biopsy device. The anatomic feature may include a bone, a vascular structure, or any other critical structure.

At block 708, a fluoroscopic sweep of at least a portion of the patient's body that includes the target and the percutaneously-inserted device inserted at the insertion point is performed to capture fluoroscopic images. At block 710, a fluoroscopic 3D reconstruction is generated based on the captured fluoroscopic images. At block 712, the fluoroscopic 3D reconstruction is registered to the preoperative CT images. The registration process may involve recognizing the same features in both the fluoroscopic 3D reconstruction and the preoperative CT images, and aligning the fluoroscopic 3D reconstruction and the preoperative CT images with each other based on the recognized features. At block 714, the markings from the preoperative CT images are transferred to the fluoroscopic 3D reconstruction based on the registering.

At block 716, an orientation of the inserted percutaneously-inserted device and a distance between the inserted percutaneously-inserted device and the target are determined based on the fluoroscopic 3D reconstruction. Then, before ending at block 724, the orientation and the distance are displayed to guide advancement of the percutaneously-inserted device toward the target at block 718.

Figure 8:
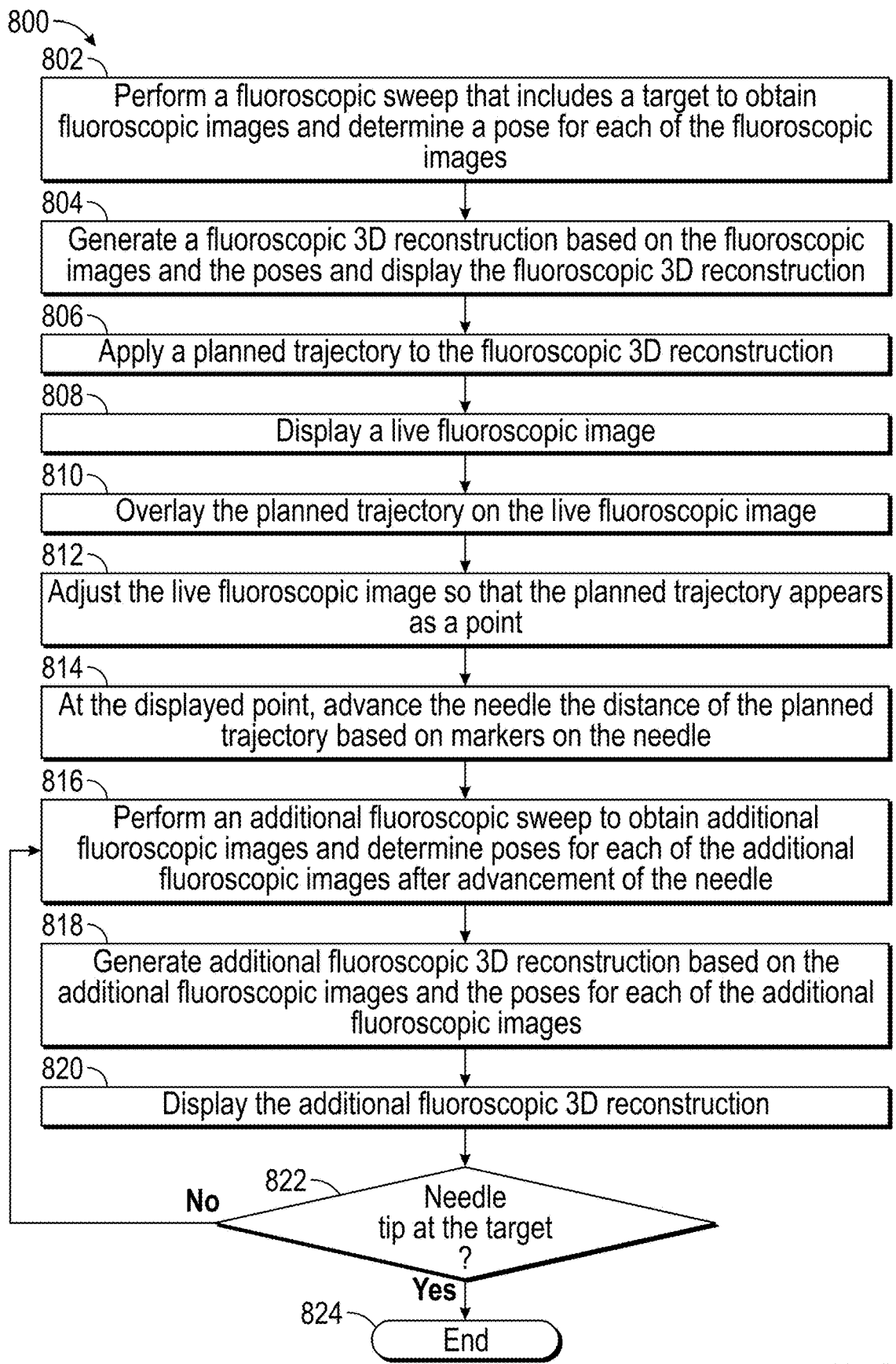
FIG. 8 is a flowchart of a method for performing a fluoroscopy-guided medical procedure in accordance with another aspect of this disclosure.

FIG. 8 is a flowchart of a method for performing a fluoroscopy-guided medical procedure in accordance with another aspect of this disclosure. At block 802, a fluoroscopic sweep of at least a portion of the patient's body that includes a target area is performed to capture fluoroscopic images, and a pose is determined for each of the fluoroscopic images. The fluoroscopic sweep may be performed after the needle is inserted at an insertion point. At block 804, a fluoroscopic 3D reconstruction is generated based on the fluoroscopic images and the poses, and the fluoroscopic 3D reconstruction is displayed. At block 806, a planned trajectory is applied to the fluoroscopic 3D reconstruction. The planned trajectory may include an insertion point, a target, and a line between the insertion point and the target. In some aspects, one or more marks indicating one or more critical structures to avoid may also be applied to, e.g., drawn on, the fluoroscopic 3D reconstruction at block 806.

At block 808, a live fluoroscopic image, which includes a view of a needle, is displayed and, at block 810, the planned trajectory, which may be indicated by one or more marks are overlaid or displayed on the live fluoroscopic image. The live fluoroscopic image may be displayed in a live fluoroscopy view or window. In some aspects, the one or more marks indicating one or more critical structures to avoid may be overlaid on the live fluoroscopic image at block 810. At block 812, the live fluoroscopic image is adjusted so that the displayed planned trajectory appears as a point or a bullseye view. Then, at block 814, at the displayed point, the needle is advanced the distance of the planned trajectory using length markers on the needle. Block 814 may include calculating and displaying a distance from the tip of the needle to the target based on the fluoroscopic 3D reconstruction of block 806. In aspects, the calculated distance may be displayed to the clinician overlaid on or adjacent to the live 2D fluoroscopy image. Then, the clinician can use the length marks on the needle to advance the needle the distance displayed to the clinician.

In aspects, one or more additional fluoroscopic sweeps are performed, and the resulting additional fluoroscopic images are processed until the needle, e.g., a biopsy device, is located at the target. For example, at block 816, an additional fluoroscopic sweep is performed to obtain additional fluoroscopic images poses for each of the additional fluoroscopic images after advancement of the needle. At block 818, an additional fluoroscopic 3D reconstruction is generated based on the additional fluoroscopic images and the poses for each of the additional fluoroscopic images, and, at block 820, the additional fluoroscopic 3D reconstruction is displayed.

At block 822, the method 800 determines whether the needle tip is located at the target. For example, the method 700 may include determining whether the clinician has clicked a button or otherwise indicated that the needle tip is or is not located at the target. If the needle tip is not located at the target, the method 800 returns to block 816 to perform an additional fluoroscopic sweep to obtain additional fluoroscopic images. Blocks 816-820 are repeated until the needle tip is located at the target. If the biopsy device is located at the target, the method 800 ends at block 824.

In some aspects, the initial sweep (e.g., the sweep of block 808) may be a full, complete, or wide sweep and the subsequent, secondary sweeps (e.g., the sweep of block 816) may be a partial or narrow sweep to, for example, minimize radiation exposure to the clinicians and/or the patient.

In aspects, location information for the biopsy device may be obtained, e.g., from the location sensor 28 disposed on the biopsy tool 27. Determining the location of the biopsy device may include generating an electromagnetic field, e.g., by the transmitter mat 56, sensing the electromagnetic field by one or more electromagnetic sensors (e.g., location sensor 28) disposed on the biopsy device, and determining the 3D coordinates of the biopsy device based on the sensed electromagnetic field. In some aspects, 3D views showing the 3D position and/or trajectory of the location sensor 28 versus the 3D position of the target may be displayed to a clinician. The clinician may use these 3D views to guide the biopsy device towards the target without a live fluoroscopy view. This may shorten the medical procedure by reducing the number of steps needed. If the target moves, additional sweeps may be performed to confirm or adjust the target position.

In some aspects, the location sensor 28 can serve as a marker, which, when using preoperative CT images, can be registered to either the navigation system or the fluoroscopic 3D reconstruction. In other aspects, when not using preoperative CT images as described herein, the location sensor 28 can be used for registering the navigation system to the fluoroscopic 3D reconstruction and the biopsy device or other percutaneously-inserted device can be navigated "on" the fluoroscopic 3D reconstruction.

Figure 9:
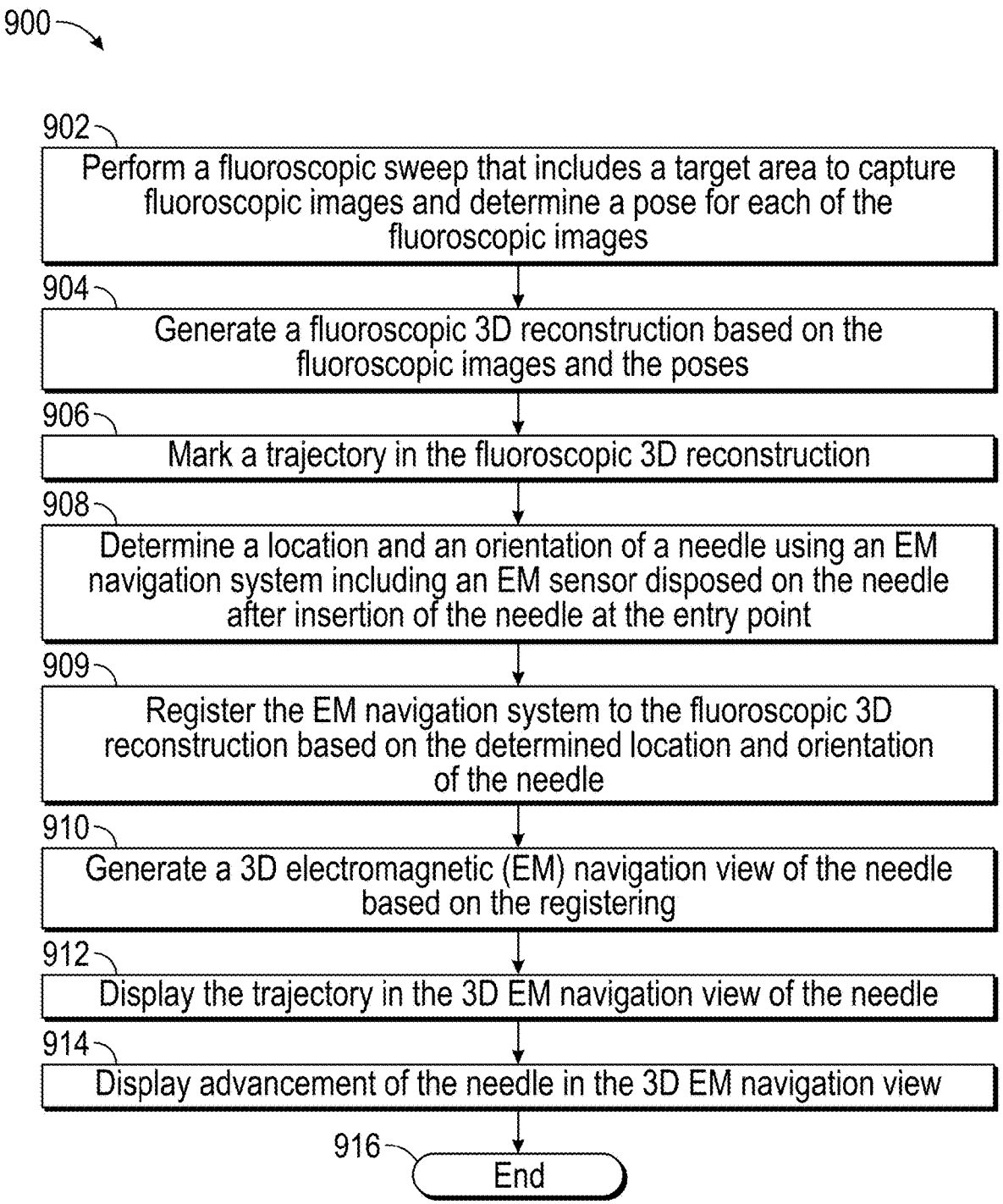
FIG. 9 is a flowchart of a method for performing an EM-guided medical procedure utilizing a marked fluoroscopic 3D reconstruction.

In aspects, information from the marked fluoroscopic 3D reconstruction may be incorporated into a 3D electromagnetic (EM) navigation view of a needle. FIG. 9 is a flowchart of a method 900 for performing an EM-guided medical procedure utilizing a marked fluoroscopic 3D reconstruction. At block 902, a fluoroscopic sweep of at least a portion of a patient's body that includes the target is performed to capture fluoroscopic images and a pose for each of the fluoroscopic images is determined. At block 904, a fluoroscopic 3D reconstruction is generated based on the fluoroscopic images and the poses.

At block 906, a trajectory, including an entry point and a target, is marked in the fluoroscopic 3D reconstruction. The method 900 may further include marking a critical structure to avoid in the fluoroscopic 3D reconstruction. Then, at block 908, a location and an orientation of a needle is determined using an EM navigation system including an EM sensor disposed on the needle, after slight insertion of the needle at the entry point. Determining the location and orientation of the needle may include generating an electromagnetic field, sensing the electromagnetic field by one or more electromagnetic sensors disposed on the needle, determining the 3D coordinates and orientation of the needle based on the sensed electromagnetic field, and generating the 3D EM navigation view based on the 3D coordinates and orientation of the needle.

At block 909, the EM navigation system is registered to the fluoroscopic 3D reconstruction based on the determined location and orientation of the needle. Registering the EM navigation system to the fluoroscopic 3D reconstruction may include identifying the EM sensor in the fluoroscopic 3D reconstruction, and registering the fluoroscopic 3D reconstruction to the 3D EM navigation view based on the identified EM sensor. At block 910, a 3D electromagnetic (EM) navigation view of the needle is generated based on the registering. The 3D EM navigation view may be generated based on the location and orientation of a needle determined by EM sensors and detectors of the EM navigation system.

At block 912, the trajectory markings are displayed in the 3D EM navigation view based on the registering. Then, before ending at block 916, advancement of the needle is displayed in the 3D EM navigation view at block 914. In aspects, the method 900 may further include performing a second fluoroscopic sweep to obtain second fluoroscopic images after navigation of the needle to the target and confirming that the needle is at the target based on the second fluoroscopic images.

In aspects, the number of iterations of performing fluoroscopic sweeps and generating the fluoroscopic 3D reconstruction depends on the location of the needle insertion or entry point and the location of the target, e.g., a lesion. For example, one iteration may be needed to get from the needle entry point to the lung, one or two iterations may be needed to verify that the needle got to the pleura, and one further iteration may be needed if the lesion is close to the pleura. If the lesion is further away from the pleura, one iteration may be needed every half inch or every inch until the needle reaches the lesion. For example, up to seven iterations may be needed to reach the lesion. And, in total, five to ten iterations may be needed to navigate the biopsy needle from the entry point to the lesion.

From the foregoing and with reference to the various figure drawings, those skilled in the art will appreciate that certain modifications can also be made to this disclosure without departing from the scope of the same. For example, although an aspect of the systems and methods is described as usable with a biopsy tool, the systems and methods described herein may be utilized with systems that utilize treatment devices, such as ablation devices. Additionally, it is appreciated that the above-described systems and methods may be utilized in other target regions such as the liver. Further, the above-described systems and methods may also be usable for transthoracic needle aspiration procedures.

Detailed embodiments of this disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ this disclosure in virtually any appropriately detailed structure.

The image-guidance systems of this disclosure may be separate from or integrated with an energy device or a separate tool and may include MRI, CT, fluoroscopy, ultrasound, electrical impedance tomography, optical, and/or device tracking systems. In aspects, the image-guided, percutaneously-inserted device may be used for biopsy, ablation, or localizing tumors, for example, with dye, a guide wire, or fiducials. Methodologies for locating the percutaneously-inserted device according to some aspects of this disclosure include electromagnetic (EM), infra-red (IR), echolocation, optical, or others. Tracking systems may be integrated to an imaging device, where tracking is done in virtual space or fused with preoperative or live images.

It should be understood that various aspects disclosed herein may be combined in different combinations than the combinations specifically presented in the description and accompanying drawings. For example, one or more of the blocks of one of FIGS. 5-9 may be combined with one or more of the block of another one of FIGS. 5-9. In a particular example, one or more of the blocks of FIG. 7 may be combined with and/or replace one or more of the blocks of FIGS. 5, 6, 8, and 9. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. For example, although the disclosure refers to a biopsy needle or tool, it is contemplated that the biopsy needle or tool may be replaced by an ablation device, a localization, or any suitable image-guided percutaneously-inserted medical device.

What is claimed is:

1. A method of performing an image-guided medical procedure, comprising:
receiving fluoroscopic images from a fluoroscopic sweep of at least a portion of a patient's body that includes a target area;
determining a fluoroscopic pose for each of the fluoroscopic images;
generating a fluoroscopic three-dimensional (3D) reconstruction based on the fluoroscopic images and the fluoroscopic poses;
applying a trajectory of a percutaneously-inserted device to the fluoroscopic 3D reconstruction such that the fluoroscopic 3D reconstruction includes a planned trajectory;
displaying a live fluoroscopic image;
overlaying the planned trajectory of the percutaneously-inserted device on the live fluoroscopic image;
displaying advancement of a percutaneously-inserted device a first distance in the live fluoroscopic image;
determining at two angles that the advancement of the percutaneously-inserted device the first distance is following the planned trajectory;
displaying advancement of the percutaneously-inserted device a second distance in response to determining at two angles that the advancement of the percutaneously-inserted device the first distance is following the planned trajectory; and
determining at two angles that the advancement of the percutaneously-inserted device the second distance is following the planned trajectory.

2. The method of claim 1, further comprising:
applying a mark indicating a critical structure to avoid to the fluoroscopic 3D reconstruction; and
overlaying the mark indicating the critical structure to avoid on the live fluoroscopic image.

3. The method of claim 1, wherein the planned trajectory includes a target, an insertion point, and a line between the insertion point and the target.

4. The method of claim 3, wherein the fluoroscopic sweep is performed after insertion of the percutaneously-inserted device at the insertion point.

5. The method of claim 1, wherein the fluoroscopic images include fluoroscopic images of a radiopaque object, further comprising:
determining the position of the radiopaque object relative to the target; and
determining the position of an insertion point based on the position of the radiopaque object relative to the target.

6. The method of claim 1, further comprising:
determining that the percutaneously-inserted device is located at the target; and
receiving one or more additional fluoroscopic images from one or more additional fluoroscopic sweeps in response to determining that the percutaneously-inserted device is not located at the target.

7. The method of claim 1, further comprising receiving preoperative computed tomography (CT) images including markings indicating the planned trajectory; and
registering the fluoroscopic 3D reconstruction to the preoperative CT images;
transferring the markings on the preoperative CT images to the fluoroscopic 3D reconstruction based on the registering; and
overlaying the fluoroscopic 3D reconstruction including the transferred marking on the live fluoroscopic image.

8. The method of claim 7, wherein the registering includes:
determining one or more anatomical features that are in both the fluoroscopic 3D reconstruction and the preoperative CT images; and
aligning the fluoroscopic 3D reconstruction and the preoperative CT images based on the determined one or more anatomical features.

9. The method of claim 8, wherein the one or more anatomical features includes the target, a lesion, a tumor, or a rib.

10. A method of performing an image-guided medical procedure, comprising:
receiving first fluoroscopic images from a first fluoroscopic sweep of at least a portion of a patient's body that includes a target area;
determining a pose for each of the first fluoroscopic images;
generating and displaying a first fluoroscopic 3D reconstruction based on the first fluoroscopic images and the poses;
marking a planned trajectory in the first fluoroscopic 3D reconstruction;
displaying a live fluoroscopic image;
overlaying the planned trajectory on the live fluoroscopic image;
adjusting the live fluoroscopic image such that the trajectory appears as a point; and
displaying advancement of a percutaneously-inserted device along the planned trajectory based on the adjusted live fluoroscopic image.

11. The method of claim 10, further comprising displaying the length of the planned trajectory,
wherein the percutaneously-inserted device is advanced based on the length of the planned trajectory and length markers on the percutaneously-inserted device.

12. The method of claim 10, wherein the planned trajectory includes an insertion point, a target, and a line between the insertion point and the target.

13. The method of claim 10, further comprising adjusting the live fluoroscopic image to a second angle to verify the depth of the percutaneously-inserted device in the patient's body.

14. The method of claim 13, further comprising adjusting the live fluoroscopic image to a third angle to verify the direction of the percutaneously-inserted device.

15. A method of performing an image-guided medical procedure, comprising:
receiving first fluoroscopic images from a first fluoroscopic sweep of at least a portion of a patient's body that includes a target area;
determining a first fluoroscopic pose for each of the first fluoroscopic images;
generating and displaying a first fluoroscopic 3D reconstruction based on the first fluoroscopic images and the first fluoroscopic poses;

applying a trajectory of a percutaneously-inserted device to the first fluoroscopic 3D reconstruction such that the first fluoroscopic 3D reconstruction includes a planned trajectory;

displaying a live fluoroscopic image;

overlaying the planned trajectory of the percutaneously-inserted device on the live fluoroscopic image;

receiving second fluoroscopic images of an insertion point from a second fluoroscopic sweep;

determining a second pose for each of the second fluoroscopic images;

generating and displaying a second fluoroscopic 3D reconstruction based on the second fluoroscopic images and the second poses; and displaying insertion of a percutaneously-inserted device in the live fluoroscopic image.

16. The method of claim 15, further comprising:

registering the second fluoroscopic 3D reconstruction to the first fluoroscopic 3D reconstruction; and transferring the planned trajectory applied to the first fluoroscopic 3D reconstruction to the second fluoroscopic 3D reconstruction based on the registering.

17. The method of claim 15, further comprising:

displaying the live fluoroscopic image in at least one fluoroscopic angle after advancement of the inserted percutaneously-inserted device a first distance; and determining that the advancement of the inserted percutaneously-inserted device the first distance is following the planned trajectory based on the live fluoroscopic image in the at least one fluoroscopic angle.

18. The method of claim 17, wherein the at least one fluoroscopic angle includes two different fluoroscopic angles at which a direction of the inserted percutaneously-inserted device can be determined from the live fluoroscopic image.

19. The method of claim 17, further comprising:

displaying the live fluoroscopic image in at least one fluoroscopic angle after advancement of the inserted percutaneously-inserted device a second distance; and determining that the advancement of the inserted percutaneously-inserted device the second distance is following the planned trajectory based on the live fluoroscopic image in the at least one fluoroscopic angle.

20. The method of claim 19, further comprising:

receiving third fluoroscopic images from a third fluoroscopic sweep after advancement of the inserted percutaneously-inserted device the second distance;

determining a third pose for each of the third fluoroscopic images; and generating and displaying a third fluoroscopic 3D reconstruction based on the third fluoroscopic images and the third poses.

* * * * *